(12) United States Patent
Jung et al.

(10) Patent No.: US 8,236,828 B2
(45) Date of Patent: Aug. 7, 2012

(54) INSECTICIDAL COMPOUNDS

(75) Inventors: Pierre Joseph Marcel Jung, Stein (FR);
Peter Renold, Stein (CH); Christopher Richard Ayles Godfrey, Stein (CH);
William Lutz, Stein (CH); Peter Maienfisch, Stein (CH); Werner Zambach, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 66 days.

(21) Appl. No.: 12/738,352

(22) PCT Filed: Oct. 13, 2008

(86) PCT No.: PCT/EP2008/008642
§ 371 (c)(1),
(2), (4) Date: Apr. 16, 2010

(87) PCT Pub. No.: WO2009/049844
PCT Pub. Date: Apr. 23, 2009

(65) Prior Publication Data
US 2010/0216850 A1     Aug. 26, 2010

(30) Foreign Application Priority Data
Oct. 17, 2007    (GB) .................................. 0720319.3

(51) Int. Cl.
*A01N 43/828*     (2006.01)
*A01N 43/80*     (2006.01)
*C07D 417/12*     (2006.01)
*C07D 261/04*     (2006.01)

(52) U.S. Cl. ......... 514/361; 514/378; 548/127; 548/240

(58) Field of Classification Search .................. 514/361, 514/378; 548/127, 240
See application file for complete search history.

(56) References Cited

FOREIGN PATENT DOCUMENTS
| | | |
|---|---|---|
| EP | 1538138 | 6/2005 |
| WO | 2007017075 | 2/2007 |
| WO | 2008012027 | 1/2008 |

*Primary Examiner* — Kamal Saeed
*Assistant Examiner* — Kristin Bianchi
(74) *Attorney, Agent, or Firm* — William A. Teoli, Jr.

(57) ABSTRACT

A compound of formula (I) wherein $A^1$, $A^2$, $A^3$, $A^4$, $G^1$, $G^2$, $R^1$, $R^2$, $R^3$, $R^4$, $Q^1$, $Y^1$, $Y^2$, $Y^3$ and $Y^4$ are as defined in claim 1; or a salt or TV-oxide thereof. Furthermore, the present invention relates to processes and intermediates for preparing compounds of formula (I), to insecticidal, acaricidal, nematicidal or molluscicidal compositions comprising them and to methods of using them to combat and control insect, acarine, nematode or mollusc pests.

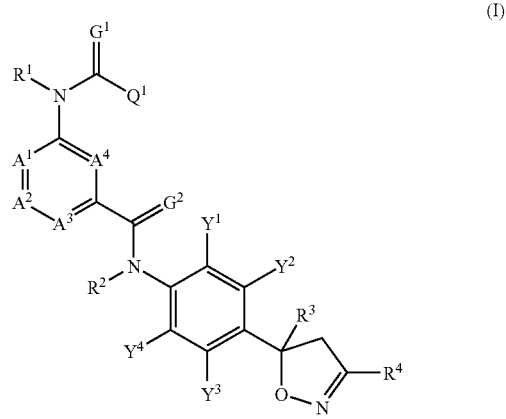

22 Claims, No Drawings

INSECTICIDAL COMPOUNDS

This application is a 371 of International Application No. PCT/EP2008/008642 filed Oct. 13, 2008, which claims priority to GB 0720319.3 filed Oct. 17, 2007, the contents of which are incorporated herein by reference.

The present invention relates to certain aromatic bisamide derivatives, to processes and intermediates for preparing them, to insecticidal, acaricidal, nematicidal or molluscicidal compositions comprising them and to methods of using them to combat and control insect, acarine, nematode or mollusc pests.

Aromatic bisamide derivatives with insecticidal properties are disclosed, for example, in EP 1,714,958, JP 2006/306771, WO 06/137376, WO 06/137395 and WO 07/017,075.

It has now surprisingly been found that certain aromatic bisamide derivatives which are substituted by an isoxazolinyl substituent have insecticidal properties.

The present invention therefore provides a compound of formula (I)

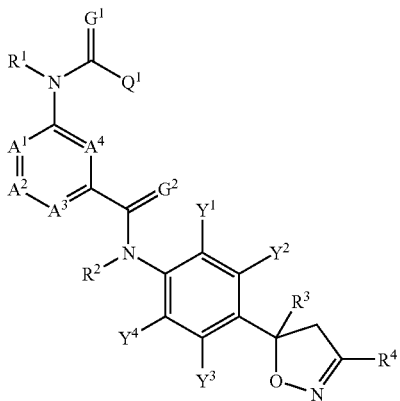

wherein
$A^1$, $A^2$, $A^3$ and $A^4$ are independently of one another C—$R^5$, C—$R^6$ or nitrogen, provided that at least one of $A^1$, $A^2$, $A^3$ and $A^4$ is C—$R^5$ and no more than two of $A^1$, $A^2$, $A^3$ and $A^4$ are nitrogen;
$G^1$ and $G^2$ are independently of each other oxygen or sulfur;
$R^1$ and $R^2$ are independently of each other hydrogen, $C_1$-$C_4$alkyl or $C_1$-$C_4$alkylcarbonyl;
$R^3$ is hydrogen, $C_1$-$C_6$alkyl, $C_1$-$C_6$haloalkyl, $C_3$-$C_6$cycloalkyl-$C_1$-$C_4$-alkyl-, $C_1$-$C_4$alkoxy-$C_1$-$C_4$-alkyl-, $C_1$-$C_4$haloalkoxy-$C_1$-$C_4$-alkyl-, $C_1$-$C_4$alkylthio-$C_1$-$C_4$-alkyl-, $C_1$-$C_4$haloalkylthio-$C_1$-$C_4$-alkyl-, $C_3$-$C_8$cycloalkyl, $C_3$-$C_8$halocycloalkyl, phenyl or phenyl substituted by one to five substituents $R^7$, which may be the same or different, 2-naphthyl or 2-naphthyl substituted by one to five substituents $R^7$, which may be the same or different, or heterocyclyl or heterocyclyl substituted by one to five substituents $R^7$, which may be the same or different;
$R^4$ is hydrogen, halogen, cyano, $C_1$-$C_6$alkyl, $C_1$-$C_6$haloalkyl, $C_3$-$C_6$cycloalkyl-$C_1$-$C_4$-alkyl-, $C_1$-$C_4$alkoxy-$C_1$-$C_4$-alkyl-, $C_1$-$C_4$haloalkoxy-$C_1$-$C_4$-alkyl-, $C_1$-$C_4$alkylthio-$C_1$-$C_4$-alkyl-, $C_1$-$C_4$haloalkylthio-$C_1$-$C_4$-alkyl-, $C_1$-$C_4$alkylsulfinyl-$C_1$-$C_4$-alkyl-, $C_1$-$C_4$haloalkylsulfinyl-$C_1$-$C_4$-alkyl-, $C_1$-$C_4$alkylsulfonyl-$C_1$-$C_4$-alkyl-, $C_1$-$C_4$haloalkylsulfonyl-$C_1$-$C_4$-alkyl-, $C_3$-$C_8$cyclo-alkyl, $C_3$-$C_8$halocycloalkyl, $C_1$-$C_6$alkoxy, $C_1$-$C_6$haloalkoxy, $C_1$-$C_6$alkylthio, $C_1$-$C_6$haloalkyl-thio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, N,N-di($C_1$-$C_6$)alkylamino, phenyl or phenyl substituted by one to five substituents $R^8$, which may be the same or different, or heterocyclyl or heterocyclyl substituted by one to five substituents $R^8$, which may be the same or different;
each $R^5$ is independently cyano, thiocyanato, aminothiocarbonyl, N—$C_1$-$C_4$alkyl-amino-thiocarbonyl or N,N-di-$C_1$-$C_4$alkyl-aminothiocarbonyl;
each $R^6$ is independently hydrogen, halogen, $C_1$-$C_4$alkyl, $C_1$-$C_4$haloalkyl or $C_1$-$C_4$alkoxy;
$Q^1$ is aryl or aryl substituted by one to five substituents $R^9$, which may be the same or different, or $Q^1$ is heterocyclyl or heterocyclyl substituted by one to five substituents $R^9$, which may be the same or different;
$Y^1$ and $Y^4$ are independently of each other hydrogen, cyano, halogen, $C_1$-$C_4$alkyl, $C_1$-$C_4$haloalkyl, $C_1$-$C_4$alkoxy-$C_1$-$C_4$-alkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl or $C_1$-$C_3$haloalkylsulfonyl;
$Y^2$ and $Y^3$ are independently of each other hydrogen, halogen or $C_1$-$C_4$alkyl; and
each $R^7$, $R^8$ and $R^9$ is independently cyano, nitro, hydroxy, halogen, $C_1$-$C_4$alkyl, $C_1$-$C_4$halo-alkyl, $C_2$-$C_4$alkenyl, $C_2$-$C_4$haloalkenyl, $C_2$-$C_4$alkynyl, $C_2$-$C_4$haloalkynyl, $C_3$-$C_6$cycloalkyl, $C_3$-$C_6$halocycloalkyl, $C_1$-$C_3$alkoxy, $C_1$-$C_3$haloalkoxy, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl, $C_1$-$C_3$haloalkylsulfonyl, $C_1$-$C_4$alkylamino, di-($C_1$-$C_4$alkyl)amino, $C_1$-$C_4$alkylcarbonyl, $C_1$-$C_4$alkylcarbonyloxy, $C_1$-$C_4$alkoxycarbonyl, $C_1$-$C_4$alkylcarbonylamino or phenyl;
or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkylcarbonyl, alkoxycarbonyl) is a straight or branched chain and is, for example, methyl, ethyl, n-propyl, iso-propyl, n-butyl, sec-butyl, iso-butyl or tert-butyl. The alkyl groups are preferably $C_1$ to $C_6$ alkyl groups, more preferably $C_1$-$C_4$ and most preferably $C_1$-$C_3$ alkyl groups.

Alkenyl and alkynyl moieties (either alone or as part of a larger group) can be in the form of straight or branched chains, and the alkenyl moieties, where appropriate, can be of either the (E)- or (Z)-configuration. Examples are vinyl, allyl and propargyl. The alkenyl and alkynyl groups are preferably $C_2$ to $C_6$ alkenyl or alkynyl groups, more preferably $C_2$-$C_4$ and most preferably $C_2$-$C_3$ alkenyl or alkynyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, trifluoromethyl, chlorodifluoromethyl, 2,2,2-trifluoro-ethyl or 2,2-difluoro-ethyl. Perfluoroalkyl groups (either alone or as part of a larger group, such as perfluoroalkylthio) are a particular type of haloalkyl group; they are alkyl groups which are completely substituted with fluorine atoms and are, for example, trifluoromethyl, pentafluoroethyl or heptafluoro-prop-2-yl.

Haloalkenyl and haloalkynyl groups (either alone or as part of a larger group) are alkenyl and alkynyl groups, respectively, which are substituted with one or more of the same or different halogen atoms and are, for example, 2,2-difluorovinyl, 1,2-dichloro-2-fluoro-vinyl or 1-chloro-prop-2-yn-1-yl-.

Cycloalkyl groups can be in mono- or bi-cyclic form and may optionally be substituted by one or more methyl groups. The cycloalkyl groups preferably contain 3 to 8 carbon atoms, more preferably 3 to 6 carbon atoms. Examples of monocyclic cycloalkyl groups are cyclopropyl, 1-methyl-cyclopropyl-, 2-methyl-cyclopropyl-, cyclobutyl, cyclopentyl and cyclohexyl.

Halocycloalkyl groups are cycloalkyl groups which are substituted with one or more of the same of different halogen atoms and may optionally be substituted by one or more methyl groups. Examples of monocyclic halocycloalkyl groups are 2,2-dichloro-cyclopropyl-, 2,2-dichloro-1-methyl-cyclopropyl- and 2-chloro-4-fluoro-cyclohexyl-.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

The term "heteroaryl" refers to an aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of such groups include pyridyl, pyridazinyl, pyrimidinyl, pyrazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. A preferred heteroaryl group is pyridine. Examples of bicyclic groups are benzothiophenyl, benzimidazolyl, benzothiadiazolyl, quinolinyl, cinnolinyl and quinoxalinyl.

The term "heterocyclyl" is defined to include heteroaryl and in addition their unsaturated or partially unsaturated analogues such as 4,5,6,7-tetrahydro-benzothiophenyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

Preferred values of $A^1$, $A^2$, $A^3$, $A^4$, $G^1$, $G^2$, $R^1$, $R^2$, $R^3$, $R^4$, $R^5$, $R^6$, $R^7$, $R^8$, $R^9$, $Q^1$, $Y^1$, $Y^2$, $Y^3$ and $Y^4$ are, in any combination, as set out below.

Preferably $A^1$ is C—$R^5$ or C—$R^6$.
Preferably $A^2$ is C—$R^5$ or C—$R^6$.
Preferably $A^3$ is C—$R^5$ or C—$R^6$.
Preferably $A^4$ is C—$R^5$ or C—$R^6$.
Preferably one, two or three of $A^1$, $A^2$, $A^3$ and $A^4$ are C—$R^5$, more preferably one or two of $A^1$, $A^2$, $A^3$ and $A^4$ are C—$R^5$, most preferably one of $A^1$, $A^2$, $A^3$ and $A^4$ is C—$R^5$.

Preferably $G^1$ is oxygen.
Preferably $G^2$ is oxygen.
Preferably $R^1$ is hydrogen, methyl, ethyl or acetyl, more preferably hydrogen, methyl or ethyl, even more preferably hydrogen or methyl, most preferably hydrogen.
Preferably $R^2$ is hydrogen, methyl, ethyl or acetyl, more preferably hydrogen, methyl or ethyl, even more preferably hydrogen or methyl, most preferably hydrogen.
Preferably $R^3$ is $C_1$-$C_6$alkyl, $C_1$-$C_6$haloalkyl, phenyl or phenyl substituted by one to five substituents $R^7$, which may be the same or different, more preferably $R^3$ is $C_1$-$C_6$alkyl or $C_1$-$C_6$haloalkyl, most preferably $R^3$ is trifluoromethyl.
Preferably $R^4$ is $C_1$-$C_6$alkyl, $C_1$-$C_6$haloalkyl, phenyl or phenyl substituted by one to five substituents $R^8$, which may be the same or different, or heterocyclyl or heterocyclyl substituted by one to five substituents $R^8$, which may be the same or different.

More preferably $R^4$ is phenyl or phenyl substituted by one to five substituents selected from halogen, $C_1$-$C_4$alkyl, $C_1$-$C_4$haloalkyl, $C_1$-$C_3$alkoxy or $C_1$-$C_3$haloalkoxy, which may be the same or different, or heterocyclyl or heterocyclyl substituted by one to five substituents selected from halogen, $C_1$-$C_4$alkyl, $C_1$-$C_4$haloalkyl, $C_1$-$C_3$alkoxy or $C_1$-$C_3$haloalkoxy, which may be the same or different.

Even more preferably $R^4$ is phenyl or phenyl substituted by one to five substituents selected from halogen, $C_1$-$C_4$alkyl, $C_1$-$C_4$haloalkyl, $C_1$-$C_3$alkoxy or $C_1$-$C_3$haloalkoxy, which may be the same or different, or heterocyclyl or heterocyclyl substituted by one to five substituents selected from halogen, $C_1$-$C_4$alkyl, $C_1$-$C_4$haloalkyl, $C_1$-$C_3$alkoxy or $C_1$-$C_3$haloalkoxy, which may be the same or different. Examples of such groups for $R^4$ are 4-bromo-phenyl, 4-chloro-phenyl, 4-cyano-phenyl, 3,4-dichloro-phenyl, 4-difluoromethoxy-phenyl, 4-fluoro-phenyl, 4-methylsulfonyloxy-phenyl, 4-methylsulfonyl-phenyl, 4-methylthio-phenyl, 4-nitro-phenyl, phenyl, 4-trifluoromethoxy-phenyl and 4-trifluoromethyl-phenyl.

Most preferably $R^4$ is phenyl or phenyl substituted by one substituent selected from halogen, $C_1$-$C_4$alkyl, $C_1$-$C_4$haloalkyl. Examples of such preferred groups for $R^4$ are 4-chloro-phenyl, 4-fluoro-phenyl and 4-trifluoromethyl-phenyl.

Preferably each $R^5$ is independently cyano, thiocyanato or aminothiocarbonyl, more preferably each $R^5$ is independently cyano or thiocyanato, most preferably each $R^5$ is cyano.

Preferably each $R^6$ is independently hydrogen, fluoro, chloro, bromo, methyl, trifluoromethyl or methoxy, more preferably hydrogen, fluoro, chloro, bromo, methyl or trifluoromethyl, even more preferably hydrogen, fluoro, methyl or trifluoromethyl, et even more preferably hydrogen or fluoro, most preferably hydrogen.

Preferably each $R^7$ is independently cyano, nitro, hydroxy, bromo, chloro, fluoro, methyl, trifluoromethyl, methoxy, trifluoromethoxy, methylthio, methylsulfinyl, methylsulfonyl or phenyl.

Preferably each $R^8$ is independently cyano, nitro, hydroxy, bromo, chloro, fluoro, methyl, trifluoromethyl, methoxy, trifluoromethoxy, methylthio, methylsulfinyl, methylsulfonyl or phenyl.

Preferably each $R^9$ is independently cyano, nitro, hydroxy, bromo, chloro, fluoro, methyl, trifluoromethyl, methoxy, trifluoromethoxy, methylthio, methylsulfinyl, methylsulfonyl or phenyl.

Preferably $Q^1$ is aryl or aryl substituted by one to five substituents $R^9$, which may be the same or different, or $Q^1$ is heteroaryl or heteroaryl substituted by one to five substituents $R^9$, which may be the same or different.

More preferably $Q^1$ is phenyl, pyridyl, furanyl, thiophenyl, pyrazolyl or 1,2,3-thiadiazolyl, or phenyl, pyridyl, furanyl, thiophenyl, pyrazolyl or 1,2,3-thiadiazolyl substituted by one to four substituents independently selected from cyano, nitro, hydroxy, bromo, chloro, fluoro, methyl, trifluoromethyl, methoxy, trifluoromethoxy, methylthio, methylsulfinyl, methylsulfonyl or phenyl, even more preferably phenyl, pyridyl, furanyl, thiophenyl, pyrazolyl or 1,2,3-thiadiazolyl, or phenyl, pyridyl, furanyl, thiophenyl, pyrazolyl or 1,2,3-thiadiazolyl substituted by one to three substituents independently selected from cyano, nitro, hydroxy, bromo, chloro, fluoro, methyl, trifluoromethyl, methoxy, methylthio, methylsulfinyl, methylsulfonyl or phenyl, yet even more preferably phenyl or pyridyl, or phenyl or pyridyl substituted by one to two substituents independently selected from cyano, hydroxy, chloro, fluoro, methyl, trifluoromethyl, methoxy, methylthio, methylsulfinyl, methylsulfonyl or phenyl, most preferably phenyl substituted by one or two substituents selected from chloro, fluoro or methyl.

A particularly preferred group of compounds are compounds of formula (I) wherein $Q^1$ is aryl or aryl substituted by one to five substituents $R^9$, which may be the same or different.

Preferably $Q^1$ is phenyl or phenyl substituted by one to four substituents independently selected from cyano, nitro, hydroxy, bromo, chloro, fluoro, methyl, trifluoromethyl, methoxy, trifluoromethoxy, methylthio, methylsulfinyl, methylsulfonyl or phenyl, more preferably phenyl or phenyl substituted by one to three substituents independently selected from cyano, nitro, hydroxy, bromo, chloro, fluoro, methyl, trifluoromethyl, methoxy, methylthio, methylsulfinyl, methylsulfonyl or phenyl, even more preferably phenyl or phenyl substituted by one to two substituents independently selected from cyano, hydroxy, chloro, fluoro, methyl, trifluoromethyl, methoxy, methylthio, methylsulfinyl, methylsulfonyl or phenyl.

Another particularly preferred group of compounds are compounds of formula (I) wherein $Q^1$ is heterocyclyl or heterocyclyl substituted by one to five substituents $R^9$, which may be the same or different. The heterocyclyl group is preferably a heteroaryl group.

Preferably $Q^1$ is pyridyl, furanyl, thiophenyl, pyrazolyl or 1,2,3-thiadiazolyl, or pyridyl, furanyl, thiophenyl, pyrazolyl or 1,2,3-thiadiazolyl substituted by one to four substituents independently selected from cyano, nitro, hydroxy, bromo, chloro, fluoro, methyl, trifluoromethyl, methoxy, trifluoromethoxy, methylthio, methylsulfinyl, methyl-sulfonyl or phenyl, more preferably pyridyl, furanyl, thiophenyl, pyrazolyl or 1,2,3-thiadiazolyl, or pyridyl, furanyl, thiophenyl, pyrazolyl or 1,2,3-thiadiazolyl substituted by one to three substituents independently selected from cyano, nitro, hydroxy, bromo, chloro, fluoro, methyl, trifluoromethyl, methoxy, methylthio, methylsulfinyl, methylsulfonyl or phenyl, even more preferably pyridyl or pyridyl substituted by one to two substituents independently selected from cyano, hydroxy, chloro, fluoro, methyl, trifluoromethyl, methoxy, methylthio, methylsulfinyl, methylsulfonyl or phenyl, most preferably pyridyl substituted by one to two substituents independently selected from chloro, fluoro or methyl.

Preferably $Y^1$ is cyano, halogen, methyl, ethyl, trifluoromethyl or methoxymethyl, more preferably cyano, bromo, chloro, methyl, ethyl, trifluoromethyl or methoxymethyl, even more preferably bromo, chloro, methyl, ethyl or methoxymethyl, yet even more preferably bromo, methyl or ethyl, even more preferably methyl or ethyl, most preferably methyl.

Preferably $Y^2$ is hydrogen, chloro, fluoro or methyl, most preferably hydrogen.

Preferably $Y^3$ is hydrogen, chloro, fluoro or methyl, most preferably hydrogen.

Preferably $Y^4$ is cyano, halogen, methyl, ethyl or trifluoromethyl, more preferably cyano, bromo, chloro, methyl, ethyl or trifluoromethyl, even more preferably bromo, chloro, methyl or ethyl, yet even more preferably bromo, methyl or ethyl, even more preferably methyl or ethyl, most preferably methyl.

One preferred embodiment are compounds of formula (Ia) wherein $A^1$ is C—CN, and $A^2$, $A^3$, $A^4$ are CH.

Another preferred embodiment are compounds of formula (Ib) wherein $A^2$ is C—CN, and $A^1$, $A^3$, and $A^4$ are CH.

A further preferred embodiment are compounds of formula (Ic) wherein $A^3$ is C—CN, and $A^1$, $A^2$, and $A^4$ are CH.

Yet another preferred embodiment are compounds of formula (Id) wherein $A^4$ is C—CN, and $A^1$, $A^2$, and $A^3$ are CH.

One preferred embodiment are compounds of formula (I) wherein $Q^2$ is 4-[3-(4-chloro-phenyl)-5-trifluoromethyl-4,5-dihydro-isoxazol-5-yl]-2,6-dimethyl-phenyl.

Another preferred embodiment are compounds of formula (I) wherein $Q^2$ is 4-[3-(4-chloro-phenyl)-5-trifluoromethyl-4,5-dihydro-isoxazol-5-yl]-2-ethyl-6-methyl-phenyl.

A further preferred embodiment are compounds of formula (I) wherein $Q^2$ is 4-[3-(4-chloro-phenyl)-5-trifluoromethyl-4,5-dihydro-isoxazol-5-yl]-2,6-diethyl-phenyl.

Yet another preferred embodiment are compounds of formula (I) wherein $Q^2$ is 4-[3-(4-chloro-phenyl)-5-trifluoromethyl-4,5-dihydro-isoxazol-5-yl]-2-methoxymethyl-6-methyl-phenyl.

One preferred embodiment are compounds of formula (I) wherein $Q^2$ is 4-[3-(4-fluoro-phenyl)-5-trifluoromethyl-4,5-dihydro-isoxazol-5-yl]-2,6-dimethyl-phenyl.

Another preferred embodiment are compounds of formula (I) wherein $Q^2$ is 4-[3-(4-fluoro-phenyl)-5-trifluoromethyl-4,5-dihydro-isoxazol-5-yl]-2-ethyl-6-methyl-phenyl.

A further preferred embodiment are compounds of formula (I) wherein $Q^2$ is 4-[3-(4-fluoro-phenyl)-5-trifluoromethyl-4,5-dihydro-isoxazol-5-yl]-2,6-diethyl-phenyl.

Yet another preferred embodiment are compounds of formula (I) wherein $Q^2$ is 4-[3-(4-fluoro-phenyl)-5-trifluoromethyl-4,5-dihydro-isoxazol-5-yl]-2-methoxymethyl-6-methyl-phenyl.

One preferred embodiment are compounds of formula (I) wherein $Q^2$ is 4-[3-(4-trifluoromethyl-phenyl)-5-trifluoromethyl-4,5-dihydro-isoxazol-5-yl]-2,6-dimethyl-phenyl.

Another preferred embodiment are compounds of formula (I) wherein $Q^2$ is 4-[3-(4-trifluoromethyl-phenyl)-5-trifluoromethyl-4,5-dihydro-isoxazol-5-yl]-2-ethyl-6-methyl-phenyl.

A further preferred embodiment are compounds of formula (I) wherein $Q^2$ is 4-[3-(4-trifluoromethyl-phenyl)-5-trifluoromethyl-4,5-dihydro-isoxazol-5-yl]-2,6-diethyl-phenyl.

Yet another preferred embodiment are compounds of formula (I) wherein $Q^2$ is 4-[3-(4-trifluoromethyl-phenyl)-5-trifluoromethyl-4,5-dihydro-isoxazol-5-yl]-2-methoxymethyl-6-methyl-phenyl.

Certain intermediates are novel and as such form a further aspect of the invention. One group of novel intermediates are compounds of formula (XII)

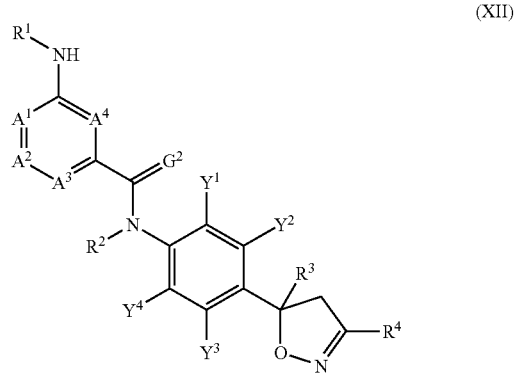

(XII)

wherein $A^1$, $A^2$, $A^3$, $A^4$, $G^2$, $R^1$, $R^2$, $R^3$, $R^4$, $Y^1$, $Y^2$, $Y^3$ and $Y^4$ are as defined in relation to formula (I); or a salt or N-oxide thereof. The preferences for $A^1$, $A^2$, $A^3$, $A^4$, $G^2$, $R^1$, $R^2$, $R^3$, $R^4$, $Y^1$, $Y^2$, $Y^3$ and $Y^4$ are the same as the preferences set out for the corresponding substituents of the compounds of the formula (I).

Another group of novel intermediates are compounds of formula (XV)

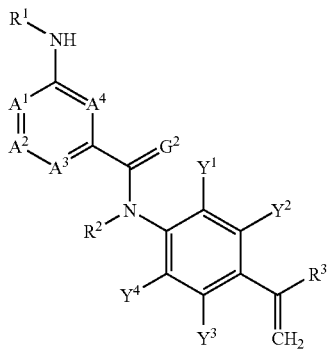
(XV)

wherein $A^1, A^2, A^3, A^4, G^2, R^1, R^2, R^3, Y^1, Y^2, Y^3$ and $Y^4$ are as defined in relation to formula (I); or a salt or N-oxide thereof. The preferences for $A^1, A^2, A^3, A^4, G^2, R^1, R^2, R^3, Y^1, Y^2, Y^3$ and $Y^4$ are the same as the preferences set out for the corresponding substituents of the compounds of the formula (I).

Another group of novel intermediates are compounds of formula (XVII)

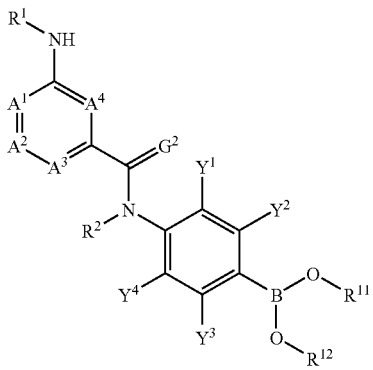
(XVII)

wherein $A^1, A^2, A^3, A^4, G^2, R^1, R^2, Y^1, Y^2, Y^3$ and $Y^4$ are as defined in relation to formula (I) and $R^{11}$ and $R^{12}$ are independently hydrogen, $C_1$-$C_6$alkyl or $C_1$-$C_6$haloalkyl, or $R^{11}$ and $R^{12}$ together with the two oxygen atoms and the boron atom through which they are connected form a five to seven-membered heterocyclyl ring, which can optionally be substituted by one to eight $C_1$-$C_4$alkyl or $C_1$-$C_4$haloalkyl groups; or a salt or N-oxide thereof. The preferences for $A^1, A^2, A^3, A^4, G^2, R^1, R^2, Y^1, Y^2, Y^3$ and $Y^4$ are the same as the preferences set out for the corresponding substituents of the compounds of the formula (I). More preferably $R^{11}$ and $R^{12}$ are independently hydrogen or $C_1$-$C_6$alkyl, or together with the two oxygen atoms and the boron atom through which they are connected form a five to seven-membered heterocyclyl ring, which can optionally be substituted by one to eight $C_1$-$C_4$alkyl groups. Most preferably $R^{11}$ and $R^{12}$ are independently hydrogen, methyl, ethyl, iso-propyl, or together with the two oxygen atoms and the boron atom through which they are connected form a five-membered heterocyclyl ring which is substituted by four methyl groups.

The compounds in Tables 1 to 12 below illustrate the compounds of the invention.

Table 1:

Table 1 provides 40 compounds of formula (Ia) wherein $R^4$ is 4-chloro-phenyl and $Q^1$ has the values listed in the table below.

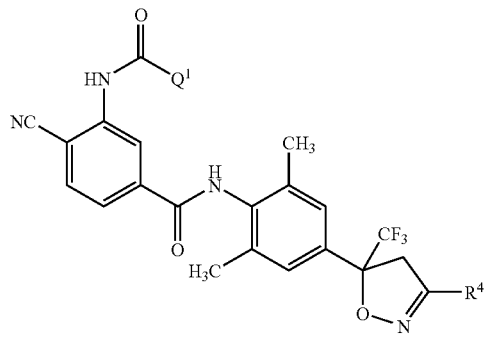
(Ia)

| Compound numbers | $Q^1$ |
|---|---|
| 1.01 | 5-bromo-furan-2-yl |
| 1.02 | 2-bromo-phenyl |
| 1.03 | 5-bromo-pyrid-3-yl |
| 1.04 | 2-chloro-4-fluoro-phenyl |
| 1.05 | 3-chloro-2-fluoro-phenyl, |
| 1.06 | 5-chloro-2-fluoro-phenyl |
| 1.07 | 3-chloro-2-methyl-phenyl |
| 1.08 | 2-chloro-4-nitro-phenyl |
| 1.09 | 2-chloro-5-nitro-phenyl |
| 1.10 | 2-chloro-phenyl |
| 1.11 | 3-chloro-phenyl |
| 1.12 | 2-chloro-pyrid-3-yl |
| 1.13 | 2-chloro-pyrid-4-yl |
| 1.14 | 6-chloro-pyrid-3-yl |
| 1.15 | 5-chloro-thiophen-2-yl |
| 1.16 | 3-chloro-5-trifluoromethyl-pyrid-2-yl |
| 1.17 | 4-cyano-2-fluoro-phenyl |
| 1.18 | 4-cyano-phenyl |
| 1.19 | 2,5-dichloro-phenyl |
| 1.20 | 2,3-difluoro-phenyl |
| 1.21 | 1,3-dimethyl-1H-pyrazol-5-yl |
| 1.22 | 2-fluoro-phenyl |
| 1.23 | 4-fluoro-phenyl |
| 1.24 | 2-fluoro-pyrid-3-yl |
| 1.25 | 2-fluoro-3-trifluoromethyl-phenyl |
| 1.26 | 2-fluoro-5-trifluoromethyl-phenyl |
| 1.27 | 4-fluoro-3-trifluoromethyl-phenyl |
| 1.28 | furan-2-yl |
| 1.29 | 2-methoxy-phenyl |
| 1.30 | 2-methyl-phenyl |
| 1.31 | 3-methyl-pyrid-2-yl |
| 1.32 | 4-methyl-1,2,3-thiadiazol-5-yl |
| 1.33 | 4-nitro-phenyl |
| 1.34 | phenyl |
| 1.35 | 1,2,3-thiadiazol-4-yl |
| 1.36 | thiophen-2-yl |
| 1.37 | 2-trifluoromethoxy-phenyl |
| 1.38 | 4-trifluoromethoxy-phenyl |
| 1.39 | 2-trifluoromethyl-phenyl |
| 1.40 | 4-trifluoromethyl-phenyl |

Table 2:
Table 2 provides 40 compounds of formula (Ia) wherein $R^4$ is 4-fluoro-phenyl and $Q^1$ has the values listed in Table 1.
Table 3:
Table 3 provides 40 compounds of formula (Ia) wherein $R^4$ is 4-trifluoromethyl-phenyl and $Q^1$ has the values listed in Table 1.
Table 4:
Table 4 provides 40 compounds of formula (Ib) wherein $R^4$ is 4-chloro-phenyl and $Q^1$ has the to values listed in Table 1.

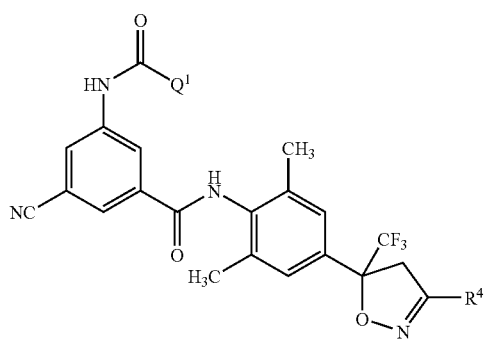

(Ib)

Table 5:
Table 5 provides 40 compounds of formula (Ib) wherein $R^4$ is 4-fluoro-phenyl and $Q^1$ has the values listed in Table 1.
Table 6:
Table 6 provides 40 compounds of formula (Ib) wherein $R^4$ is 4-trifluoromethyl-phenyl and $Q^1$ has the values listed in Table 1.
Table 7:
Table 7 provides 40 compounds of formula (Ic) wherein $R^4$ is 4-chloro-phenyl and $Q^1$ has the values listed in Table 1.

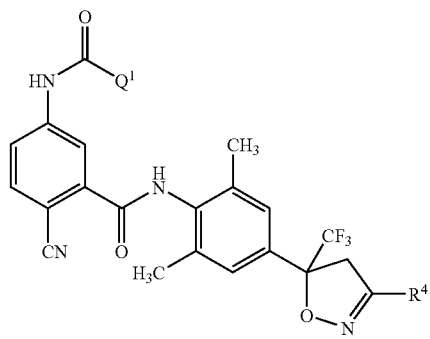

(Ic)

Table 8:
Table 8 provides 40 compounds of formula (Ic) wherein $R^4$ is 4-fluoro-phenyl and $Q^1$ has the values listed in Table 1.
Table 9:
Table 9 provides 40 compounds of formula (Ic) wherein $R^4$ is 4-trifluoromethyl-phenyl and $Q^1$ has the values listed in Table 1.
Table 10:
Table 10 provides 40 compounds of formula (Id) wherein $R^4$ is 4-chloro-phenyl and $Q^1$ has the values listed in Table 1.

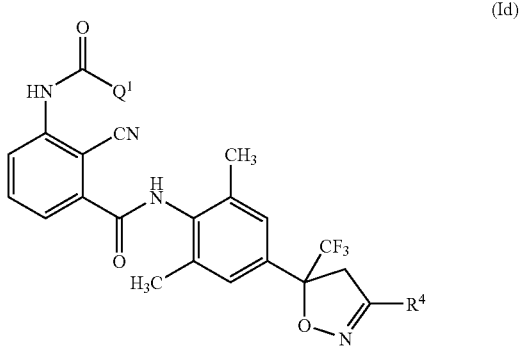

(Id)

Table 11:
Table 11 provides 40 compounds of formula (Id) wherein $R^4$ is 4-fluoro-phenyl and $Q^1$ has the values listed in Table 1.
Table 12:
Table 12 provides 40 compounds of formula (Id) wherein $R^4$ is 4-trifluoromethyl-phenyl and $Q^1$ has the values listed in Table 1.

The compounds of the invention may be made by a variety of methods.

1) Compounds of formula (I), wherein $G^1$ and $G^2$ are oxygen, may be made by treatment of a compound of formula (II), wherein $G^1$ and $G^2$ are oxygen, with a hydroxyl-oxime of formula (III) in a two step process.

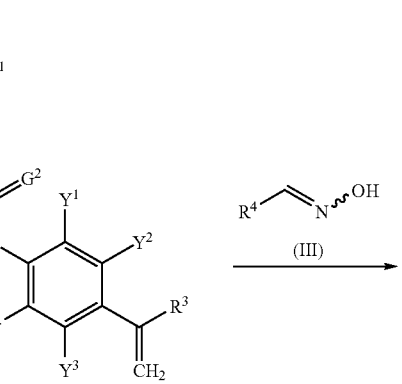 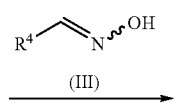

(II)

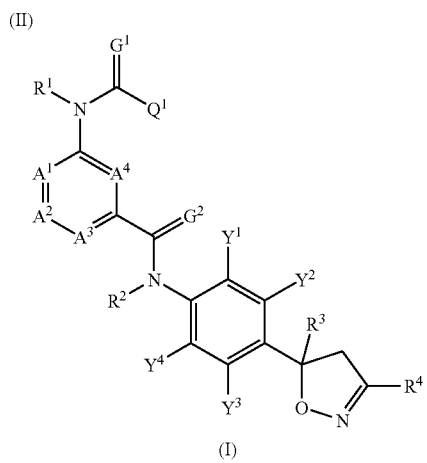

(I)

First the hydroxyl-oxime of formula (III) is reacted with a halogenating agent, such as N-chlorosuccinimide, to form a vinyl halide. Then the vinyl halide is reacted with a compound to of formula (II) in the presence of a base, such as triethylamine. Such procedures are known, for example, from Indian Journal of Chemistry, Section B (1993), 32B (4), 471-474; and Current Organic Chemistry (2005), 9(10), 925-958. Hydroxyl-oximes of formula (III) are commercially available or may be made by methods known to a person skilled in the art.

2) Compounds of formula (II), wherein $G^1$ and $G^2$ are oxygen, may be made by treatment of a compound of formula (IV), wherein $G^1$ is oxygen and R is OH, $C_1$-$C_6$alkoxy or Cl, F or Br with an amine of formula (V).

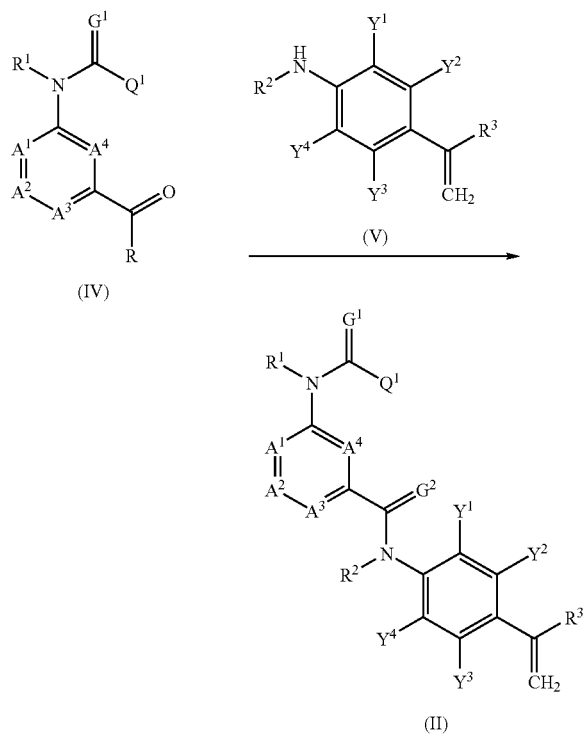

When R is OH such reactions are usually carried out in the presence of a coupling reagent, such as N,N'-dicyclohexyl-carbodiimide ("DCC"), 1-ethyl-3-[3-dimethylamino-propyl]-carbodiimide hydrochloride ("EDC") or bis(2-oxo-3-oxazolidinyl)phosphonic chloride ("BOP-Cl"), in the presence of a base, such as pyridine, triethylamine, 4-(dimethylamino)-pyridine or diisopropylethylamine, and optionally in the presence of a nucleophilic catalyst, such as hydroxybenzotriazole. When R is Cl, such reactions are usually carried out under basic conditions (for example in the presence of pyridine, triethylamine, 4-(dimethylamino)-pyridine or diisopropylethylamine), again optionally in the presence of a nucleophilic catalyst. Alternatively, it is possible to conduct the reaction in a biphasic system comprising an organic solvent, preferably ethyl acetate, and an aqueous solvent, preferably a solution of sodium bicarbonate. When R is $C_1$-$C_6$alkoxy it is sometimes possible to convert the ester directly to the amide by heating the ester and amine together in a thermal process.

3) Acid halides of formula (IV), wherein $G^1$ is oxygen and R is Br, Cl or F, may be made from a carboxylic acid of formula (IV), wherein $G^1$ is oxygen and R is OH, under standard conditions, such as treatment with thionyl chloride or oxalyl chloride.

4) Carboxylic acids of formula (IV), wherein $G^1$ is oxygen and R is OH, may be formed from an ester of formula (IV), wherein $G^1$ is oxygen and R is $C_1$-$C_6$alkoxy. It is known to a person skilled in the art that there are many methods for the hydrolysis of such esters depending on the nature of the alkoxy group. One widely used method to achieve such a transformation is the treatment of the ester with an alkali hydroxide, such as sodium hydroxide, in a solvent, such as ethanol.

5) Amines of formula (V) may be made from an amine of formula (VI) wherein $X^A$ is a leaving group such as a halogen, preferably bromine, in a two step process. First the amine of formula (VI) is reacted with a boron reagent of the formula $[B(OR^{11})(OR^{12})]_2$ wherein $R^{11}$ and $R^{12}$ are independently hydrogen, $C_1$-$C_6$alkyl or $C_1$-$C_6$haloalkyl, or $R^{11}$ and $R^{12}$ together with the two oxygen atoms and the boron atom through which they are connected form a five to seven-membered heterocyclyl ring, which can optionally be substituted by one to eight $C_1$-$C_4$alkyl or $C_1$-$C_4$haloalkyl groups, such as bis(pinacolato)diboron, in the presence of a catalyst/ligand system, often a palladium(II) complex, in the presence of a base under an inert atmosphere. Such procedures are known, for example, from Palladium(0)-Catalyzed Cross-Coupling Reaction of Alkoxydiboron with Haloarenes: A Direct Procedure for Arylboronic Esters; Ishiyama, Tatsuo; Murata, Miki; Miyaura, Norio; and Journal of Organic Chemistry (1995), 60(23), 7508-10.

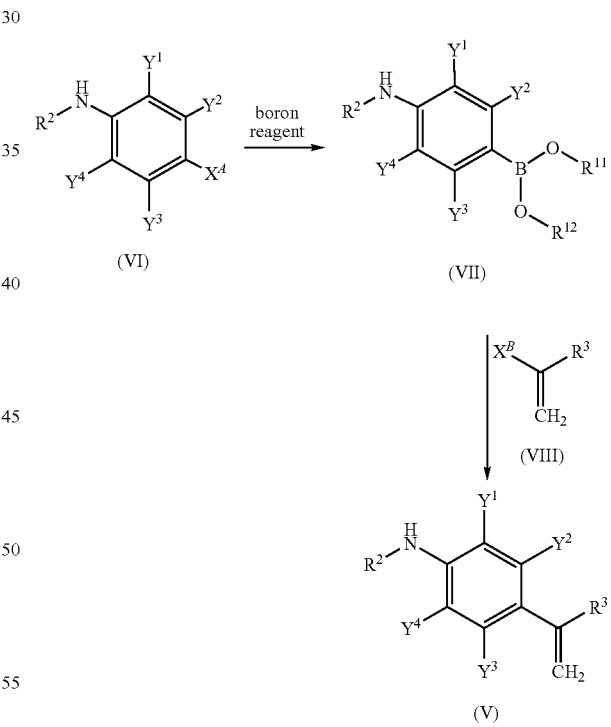

The boronic ester of formula (VII) is then reacted with a vinyl halide of formula (VIII) in the presence of a suitable catalyst/ligand system, often a palladium(II) complex, in the presence of a base under an inert atmosphere. Such procedures are known, for example, from WO 02/08221. Amines of formula (VI) are commercially available or may be made by methods known to a person skilled in the art. Vinyl halides of formula (VIII) are commercially available or may be made by methods known to a person skilled in the art.

6) Compounds of formula (IV), wherein $G^1$ is oxygen and R is $C_1$-$C_6$alkoxy, may be made from of an amine of formula (IX), wherein R is $C_1$-$C_6$alkoxy, by acylation with a carboxylic acid of formula $Q^1$-COOH or an acid halide of formula $Q^1$-COHal, wherein Hal is Br, Cl or F, under standard conditions as described in 2).

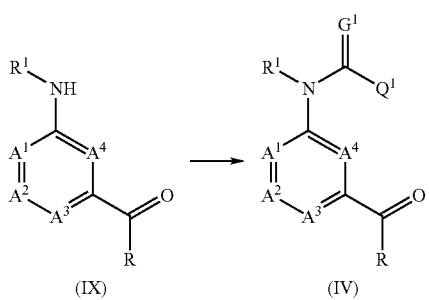

(IX) (IV)

7) For amines of formula (IX), the esters (wherein R is $C_1$-$C_6$alkoxy) may be hydrolysed to the acids (wherein R is OH) by treatment with an alkali hydroxide, such as sodium hydroxide, in a solvent, such as ethanol as described in 4). The acids (wherein R is OH) may be converted to the acid chlorides (wherein R is Cl) by treatment with thionyl chloride or oxalyl chloride as described in 3).

8) Amines of formula (IX), wherein R is $C_1$-$C_6$alkoxy, may be made from an amine of formula (X) by sequential treatment with an alcohol R—OH under acidic conditions and then formation of the N—$R^1$ bond. It is known to a person skilled in the art that there are many reported methods for the formation of this bond depending on the nature of the substituent $R^1$.

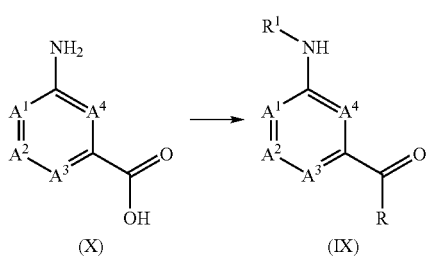

(X) (IX)

For example, reductive amination may be achieved by treatment of the amine with an aldehyde or ketone and a reducing agent such as sodium cyanoborohydride. Alternatively, alkylation may be achieved by treating the amine with an alkylating agent such as an alkyl halide, optionally in the presence of a base. Alternatively, arylation may be achieved by treatment of the amine with an aryl halide or sulfonate in the presence of a suitable catalyst/ligand system, often a palladium(0) complex. Compounds of formula (X) are commercially available or may be made by methods known to a person skilled in the art.

9) Alternatively, compounds of formula (I), wherein $G^1$ and $G^2$ are oxygen, may be made from an amine of formula (XII), wherein $G^2$ is oxygen, by acylation with a carboxylic acid of formula $Q^1$-COOH or an acid halide of formula $Q^1$-COHal, wherein Hal is Br, Cl or F, under standard conditions as described in 2).

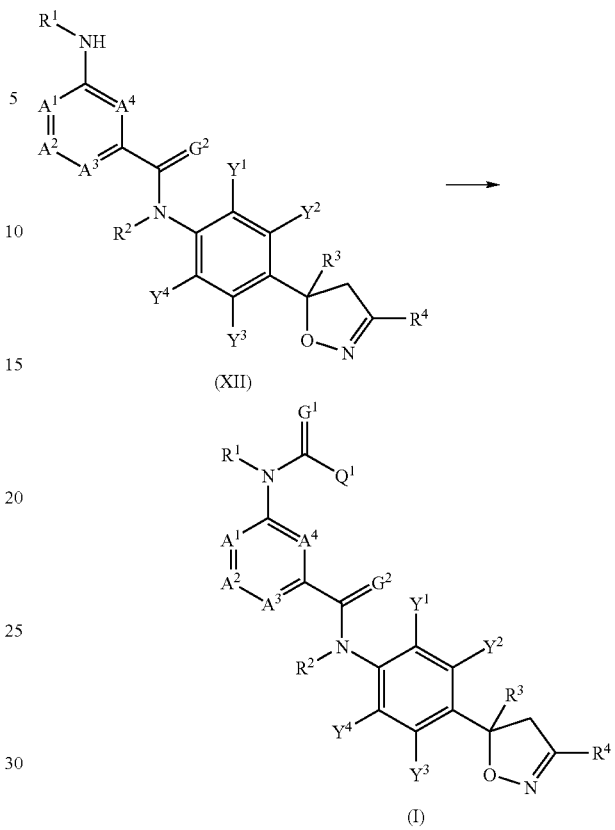

10) Amines of formula (XII), wherein $G^2$ is oxygen and $R^1$ is hydrogen, may be made by the reduction of a nitro compound of formula (XIII), wherein $G^2$ is oxygen.

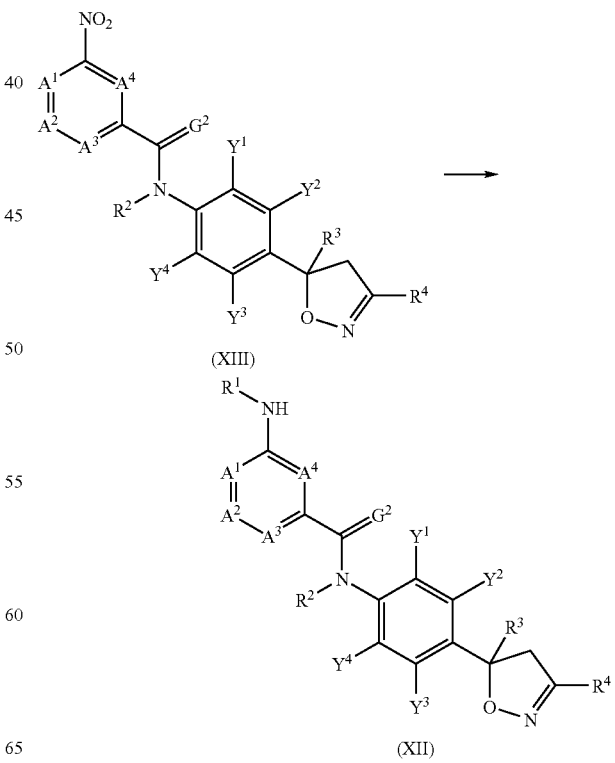

There are numerous methods for achieving such a transformation reported in the literature such as treatment with tin chloride under acidic conditions, or hydrogenation catalysed by a noble metal such as palladium on carbon.

11) Compounds of formula (XIII), wherein $G^2$ is oxygen, may be made by treatment of a compound of formula (XIV), wherein $G^2$ is oxygen, with a hydroxyl-oxime of formula (III) in a two step process as described in 1).

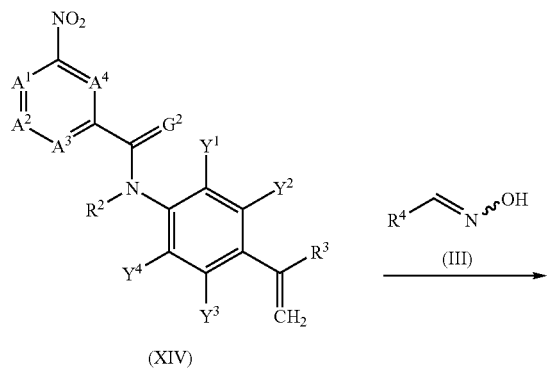

12) Compounds of formula (XIV), wherein $G^2$ is oxygen, may be made by treatment of a compound of formula (XV), wherein $G^2$ is oxygen and R is OH, $C_1$-$C_6$alkoxy or Cl, F or Br with an amine of formula (V) under standard conditions as described in 2).

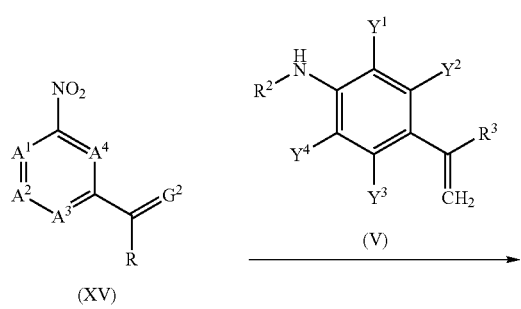

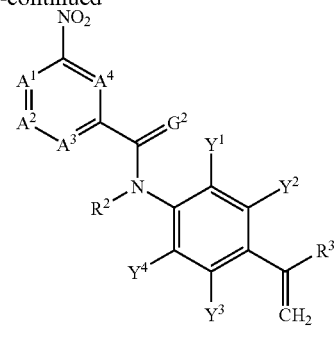

Compounds of formula (XV) are commercially available or may be made by methods known to a person skilled in the art.

13) For compounds of formula (XV), the esters (wherein R is $C_1$-$C_6$alkoxy) may be hydrolysed to the acids (wherein R is OH) by treatment with an alkali hydroxide, such as sodium hydroxide, in a solvent, such as ethanol as described in 4). The acids (wherein R is OH) may be converted to the acid chlorides (wherein R is Cl) by treatment with thionyl chloride or oxalyl chloride as described in 3).

14) Alternatively, compounds of formula (XII), wherein $G^2$ is oxygen, may be made by treatment of a compound of formula (XV), wherein $G^2$ is oxygen, with a hydroxyl-oxime of formula (III) in a two step process as described in 1).

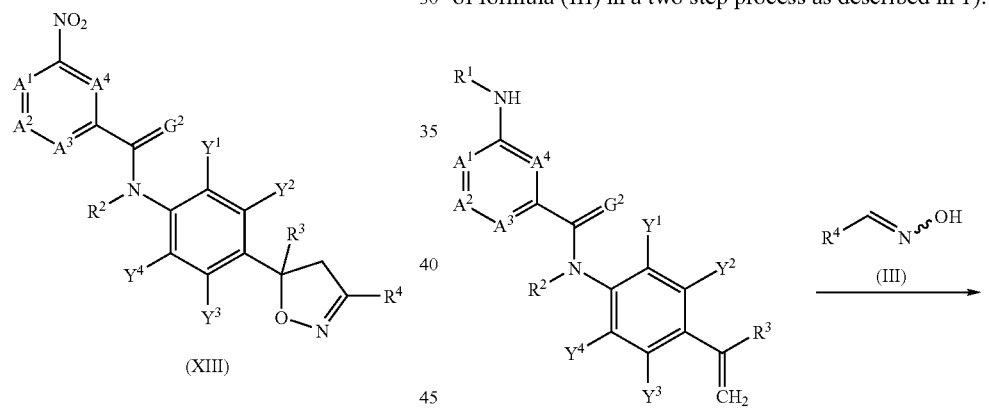

15) Amines of formula (XV), wherein $G^2$ is oxygen, may be made by treatment of an amine of formula (XVI), wherein $G^2$ is oxygen and $X^A$ is a leaving group such as a halogen, preferably bromine, in a two step process as described in 5).

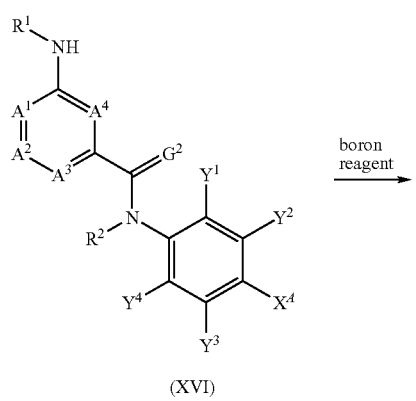

(XVI)

boron reagent →

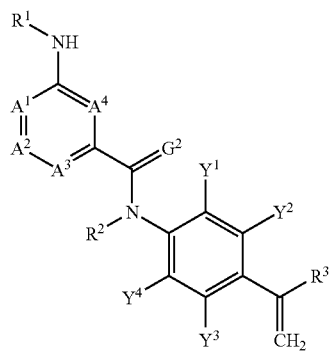

(XVII)

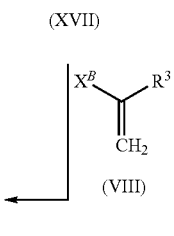

(VIII)

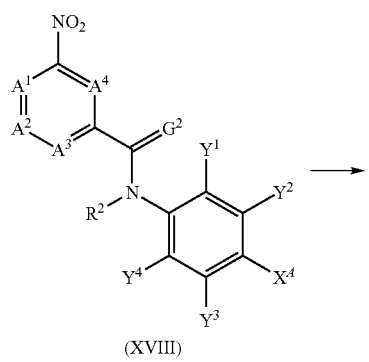

(XV)

16) Amines of formula (XVI), wherein $G^2$ is oxygen and $R^1$ is hydrogen, may be made by the reduction of a nitro compound of formula (XVIII), wherein $G^2$ is oxygen, as described in 10).

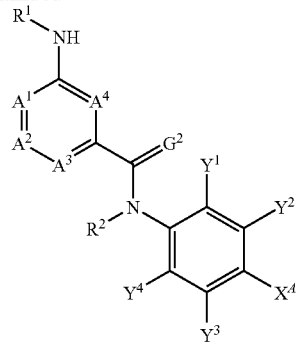

(XVI)

17) Nitro compounds of formula (XVIII), wherein $G^2$ is oxygen, may be made by treatment of a compound of formula (XV), wherein R is OH, $C_1$-$C_6$alkoxy or Br, Cl or F with an amine of formula (VI) under standard conditions as described in 2).

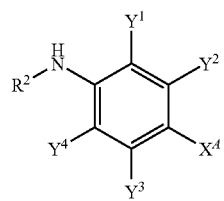

(XV)         (VI)

→

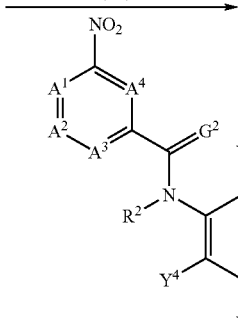

(XVIII)

18) Compounds of formula (I), wherein $G^1$ and $G^2$ are sulfur, may be made from a compound of formula (I), wherein $G^1$ and $G^2$ are oxygen, by treatment with a thio-transfer reagent, such as Lawesson's reagent or phosphorus pentasulfide.

19) Compounds of formula (I), wherein $G^1$ is oxygen and $G^2$ is sulfur, may be made from a compound of formula (XII), wherein $G^2$ is oxygen, by treatment with a thio-transfer reagent, such as Lawessen's reagent or phosphorus pentasulfide, prior to acylation with a carboxylic acid of formula $Q^1$-COOH or an acid halide of formula $Q^1$-COHal, wherein Hal is Cl, F or Br.

20) Compounds of formula (XV) wherein $R^5$ is cyano, can be made from a compound of formula (XV') wherein LG is halogen, such as fluorine or chlorine, by reaction with a cyanide salt, such as potassium cyanide, in the presence of a base, such as potassium carbonate.

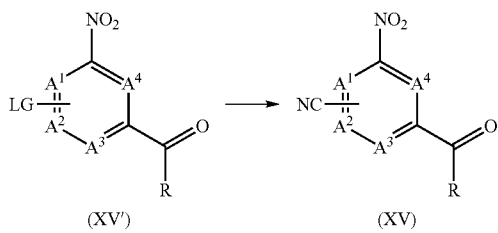

(XV')    (XV)

The displacement of a halogen with cyanide can also be carried out on intermediates of formula (XIII). Likewise compounds of formula (XV) and (XIII) wherein $R^5$ is thiocyanato, can be made from a compound of formula (XV') or (XIII') wherein LG is halogen, such as iodine, fluorine or chlorine, by reaction with a thiocyanato salt, such as potassium thiocyanate or copper thiocyanate as described for example in Journal of the Chemical Society, Chemical Communications, (2), 8102; 1989 or Synthetic Communications, 10(8), 633-6; 1980.

21) Compounds of formula (XV) wherein $R^5$ is cyano, can be made from a compound of formula (XV') wherein LG is an amine, by reaction with a cyanide salt, such as copper cyanide, via diazotising reaction. The displacement of an amine with cyanide can also be carried out on intermediates of formula (XIII).

22) Compounds of formula (I), wherein $G^1$ and $G^2$ are oxygen and $R^5$ is amino-thiocarbonyl, can be made, for example, by treatment of a compound of formula (I) wherein $R^5$ is cyano with $P_4S_{10}$ or $H_2S$ as described, for example, in Journal of Fluorine Chemistry (2006), 127(1), 63-67, and Synthesis (2006), (2), 224-226 or Synthetic Communications (2003), 33(24), 4279-4284. Alternatively, compounds of formula (I), wherein $G^1$ and $G^2$ are oxygen and $R^5$ is aminothiocarbonyl can be made, for example, by treatment of a compound of formula (I), wherein $R^5$ is cyano by reaction with sodium hydrogen sulfide and magnesium chloride as described, for example, in Synthetic Communications (2005), 35(5), 761-764.

23) Compounds of formula (I), wherein $G^1$ and $G^2$ are oxygen and $R^5$ is N-$C_1$-$C_4$alkyl-aminothiocarbonyl can be made, for example, by treatment of a compound of formula (I), wherein $G^1$ and $G^2$ are oxygen and $R^5$ is aminothiocarbonyl by reaction with an N-$C_1$-$C_4$alkyl-amine, as described, for example, in U.S. Pat. No. 5,049,669 or Journal of Sulfur Chemistry (2006), 27(3), 203-212.

24) Compounds of formula (I), wherein $G^1$ and $G^2$ are oxygen and $R^5$ is N,N-di-$C_1$-$C_4$alkyl-aminothiocarbonyl can be made, for example, by treatment of a compound of formula (I), wherein $G^1$ and $G^2$ are oxygen and $R^5$ is cyano by reaction with an N,N-di-$C_1$-$C_4$alkyl-amine in the presence of sulfur, preferably with microwave irradiation, as described, for example, in Synthetic Communications (2003), 33(24), 4279-4284. Alternatively, compounds of formula (I), wherein $G^1$ and $G^2$ are oxygen and $R^5$ is N,N-di-$C_1$-$C_4$alkyl-aminothiocarbonyl can be made, for example, by treatment of a compound of formula (I), wherein $G^1$ and $G^2$ are oxygen and $R^5$ is cyano by reaction with an N,N-di-$C_1$-$C_4$alkyl-dithiocarbamate as described, for example, in Bulletin of the Chemical Society of Japan (1967), 40(9), 2209.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus lotus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B8 (cotton), Bollgard® (cotton), NewLeaf® (potatoes), NatureGard® and Protexcta®

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavour).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifiying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures preferably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:
a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;
b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron or chlorfluazuron;
e) Organic tin compounds, such as cyhexatin, fenbutatin oxide or azocyclotin;
f) Pyrazoles, such as tebufenpyrad and fenpyroximate;
g) Macrolides, such as avermectins or milbemycins, for example abamectin, emamectin benzoate, ivermectin, milbemycin, spinosad or azadirachtin;
h) Hormones or pheromones;
i) Organochlorine compounds such as endosulfan, benzene hexachloride, DDT, chlordane or dieldrin;
j) Amidines, such as chlordimeform or amitraz;
k) Fumigant agents, such as chloropicrin, dichloropropane, methyl bromide or metam;
l) Neonicotinoid compounds such as imidacloprid, thiacloprid, acetamiprid, nitenpyram, dinotefuran or thiamethoxam;
m) Diacylhydrazines, such as tebufenozide, chromafenozide or methoxyfenozide;
n) Diphenyl ethers, such as diofenolan or pyriproxifen;
o) Indoxacarb;
p) Chlorfenapyr;
q) Pymetrozine;
r) Spirotetramat, spirodiclofen or spiromesifen; or
s) Flubendiamid or rynaxypyr In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5-dimethyl-2-trimethylsilylthiophene-3-carboxamide (MON65500), N-(1-cyano-1,2-dimethylpropyl)-2-(2,4-dichlorophenoxy) propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenoquat, diflumetorim, O,O-diiso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N-([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

PREPARATION EXAMPLES

Example I1

Preparation of N-(4-bromo-2,6-dimethyl-phenyl)-4-fluoro-3-nitro-benzamide

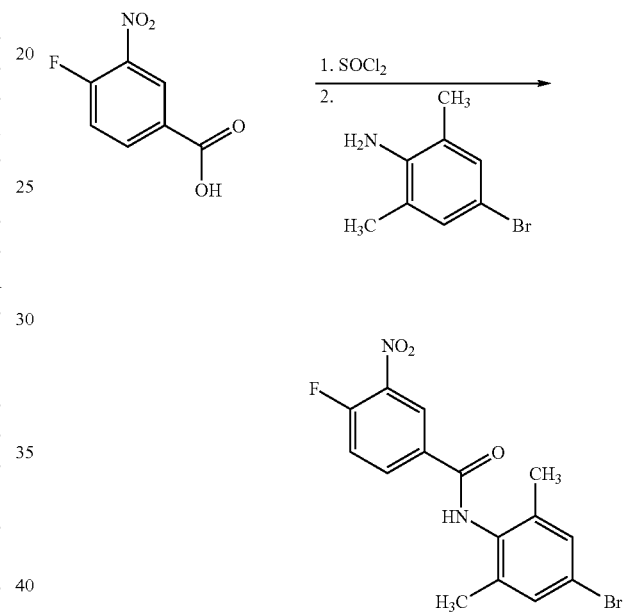

Step A: A suspension of 4-fluoro-3-nitrobenzoic acid (18.5 g, 100 mmol) in thionyl chloride (23.79 g) was stirred at 85° C. under an atmosphere of nitrogen for 16 hours. The reaction mixture was allowed to cool to ambient temperature and was concentrated. The residue, 4-fluoro-3-nitrobenzoyl chloride, was dissolved in anhydrous tetrahydrofuran (10 ml) and the solution was used without further purification.

Step B: To a mixture of 4-bromo-2,6-dimethylaniline (15 g, 75 mmol) (commercially available) and pyridine (16.1 ml, 200 mmol) in anhydrous tetrahydrofuran (150 ml) under an atmosphere of nitrogen was added the solution of 4-fluoro-3-nitrobenzoyl chloride (Step A). The reaction mixture was stirred at ambient temperature for 8 hours. The reaction mixture was diluted with ethyl acetate and aqueous sodium hydrogen carbonate (saturated). The phases were separated and the aqueous phase was extracted twice with ethyl acetate. The combined organic phases were dried over sodium sulfate and concentrated. The residue was purified by column chromatography on silica gel (eluent: cyclohexane/ethyl acetate 2:1) to give N-(4-bromo-2,6-dimethyl-phenyl)-4-fluoro-3-nitro-benzamide (27.54 g, 67% yield) which was used without further purification. LC/MS (Method A): 369 (MH$^+$), 410 (MH$^+$+CH$_3$CN).

Example I2

Preparation of N-(4-bromo-2,6-dimethyl-phenyl)-4-cyano-3-nitro-benzamide

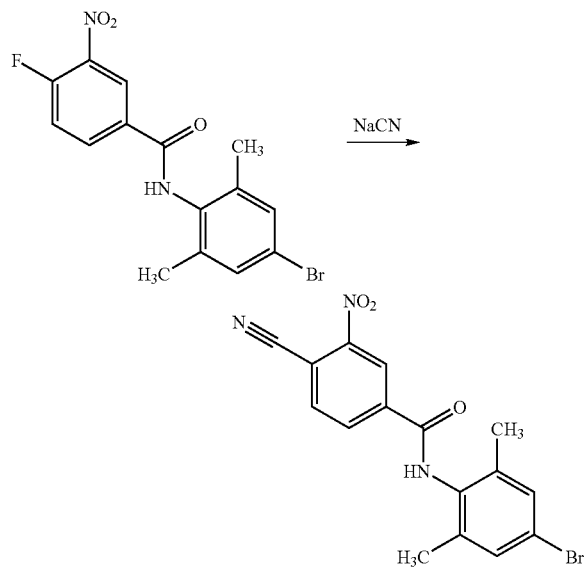

To a solution of N-(4-bromo-2,6-dimethyl-phenyl)-4-fluoro-3-nitro-benzamide (18.3 g, 49.8 mmol) (Example I1) in N,N-dimethylformamide (115 ml) was added sodium cyanide (2.7 g, 54.8 mmol). The reaction mixture was stirred at ambient temperature for 4 hours, then heated to 60° C. for 16 hours. More sodium cyanide (0.73 g, 14.8 mmol) was added and the reaction mixture was heated to 60° C. for a further 8 hours. The reaction mixture was cooled to ambient temperature before the addition of water (200 ml) and ethyl acetate (100 ml). The organic extract was washed with water and brine, dried over sodium sulfate and concentrated. The residue was purified by column chromatography on silica gel (eluent: cyclohexane/ethyl acetate 3:1), yielding N-(4-bromo-2,6-dimethyl-phenyl)-4-cyano-3-nitro-benzamide (11.8 g, 63% yield). LC/MS (Method A): 374 (MH$^+$). $^1$H-NMR (400 MHz, DMSO-d$_6$): 8.91 (s, 1H), 8.53 (d, 1H), 8.4 (d, 1H), 7.4 (s, 2H), 2.2 (s, 6H) ppm.

Example I3

Preparation of 3-amino-N-(4-bromo-2,6-dimethyl-phenyl)-4-cyano-benzamide

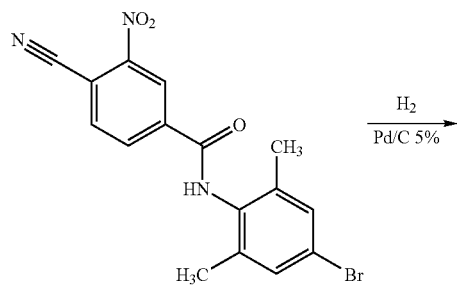

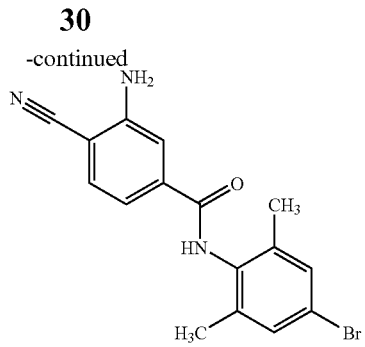

To a solution of N-(4-bromo-2,6-dimethyl-phenyl)-4-fluoro-3-nitro-benzamide (11.32 g) (Example I2) in a mixture of toluene (120 ml) and water (12 ml) was added palladium on charcoal (5% by weight) (180 mg). The reactor was charged with hydrogen (1.8 l, 10 bar) and the reaction mixture was heated to 80° C. for 4.5 hours. The reaction mixture was cooled to ambient temperature and then filtered to remove the palladium catalyst. The filtrate was concentrated. The residue was purified by column chromatography on silica gel (eluent: cyclohexane/ethyl acetate 3:1) to give 3-amino-N-(4-bromo-2,6-dimethyl-phenyl)-4-cyano-benzamide (5.9 g, 55% yield). LC/MS (Method A): 346 (MH$^+$), 387 (MH$^+$+CH$_3$CN); RT: 1.66. $^1$H-NMR (CDCl$_3$, 400 MHz): 7.53 (d, 1H), 7.24-7.34 (m, 3H), 7.18 (d, 1H), 4.63 (s, 2H), 2.24 (s, 2H) ppm.

Example I4

Preparation of 3-amino-4-cyano-N-[2,6-dimethyl-4-(4,4,5,5-tetramethyl-[1,3,2]dioxaborolan-2-yl)-phenyl]-benzamide

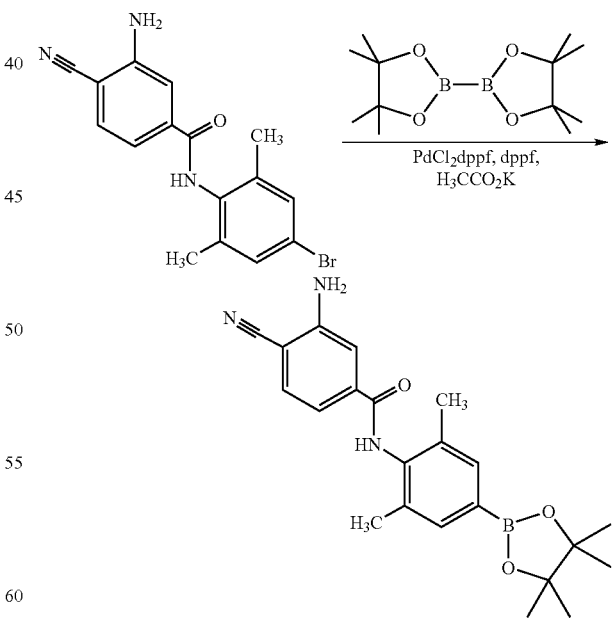

3-Amino-N-(4-bromo-2,6-dimethyl-phenyl)-4-cyano-benzamide (6.7 g, 19.5 mmol) (Example I3), bis(pinacolato)diboron (5.44 g, 21.4 mmol), 1,1'-bis(diphenylphosphino)-ferrocene palladium(II) dichloride ("PdCl$_2$dppf") (crystallised with dichloromethane 1:1) (0.318 g, 0.39 mmol), 1,1'-bis(diphenylphosphino)ferrocene ("dppf") (0.22 g, 0.39 mmol) and potassium acetate (5.73 g, 58.38 mmol) were dissolved under an argon atmosphere in absolute dioxane (60 ml). The reaction mixture was heated to 80° C. for 18 hours. The reaction mixture was allowed to cooled ambient temperature and filtered through a plug of Celite®. The filtrate was diluted with water (100 ml) and dichloromethane (100 ml) and the phases were separated. The organic phase was washed twice with water, and aqueous phases were extracted twice with dichloromethane. The combined organic phases were dried over sodium sulfate and concentrated. The residue was purified by column chromatography on silica gel (eluent: hexane/ethyl acetate 4:1) to give 3-amino-4-cyano-N-[2,6-dimethyl-4-(4,4,5,5-tetramethyl-[1,3,2]dioxaborolan-2-yl)-phenyl]-benzamide (6.88 g, 90% yield). $^1$H-NMR (CDCl$_3$, 400 MHz): 7.62 (s, 2H), 7.55 (d, 1H), 7.37 (m, 2H), 7.2 (d, 1H), 4.62 (s, 2H), 2.30 (s, 6H), 1.4 (s, 12H) ppm.

Example I5

Preparation of 3-amino-4-cyano-N-[2,6-dimethyl-4-(1-trifluoromethyl-vinyl)-phenyl]-benzamide

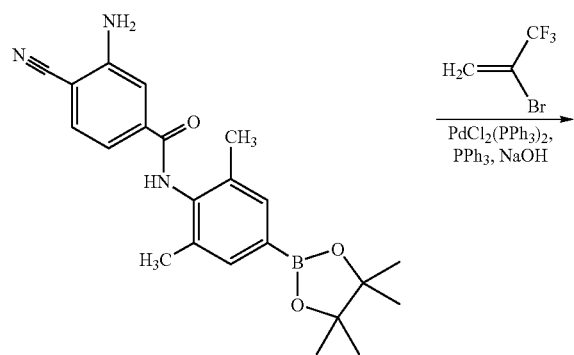

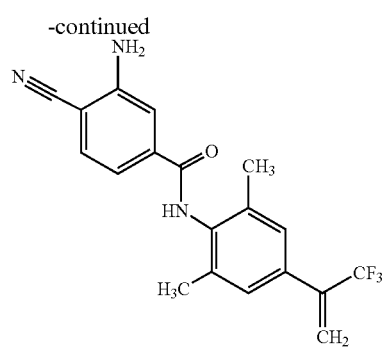

3-Amino-4-cyano-N-[2,6-dimethyl-4-(4,4,5,5-tetramethyl-[1,3,2]dioxaborolan-2-yl)-phenyl]-benzamide (6 g, 15.3 mmol) (Example I4) was dissolved in a mixture of 1,2-dimethoxyethane (22 ml) and tetrahydrofuran (22 ml) in a microwave vial. Then, at 0° C. under an argon atmosphere, 2-bromo-3,3,3-trifluoro-propene (3.20 ml, 30.6 mmol), bis(triphenylphosphine) palladium(II) dichloride (PdCl$_2$(PPh$_3$)$_2$) (0.32 g, 0.46 mmol) and triphenylphosphine (0.6 g, 2.29 mmol) were added. Finally, an aqueous solution of sodium hydroxide (2M) (30 ml) was added at 0° C. under an argon atmosphere. The vial was sealed and heated to 130° C. for 10 minutes in a microwave oven. The reaction mixture was allowed to cool to ambient temperature and concentrated. The residue was suspended in ethyl acetate (500 ml) and filtered through a plug of Celite®. The filtrate was washed twice with water (500 ml). The aqueous phases were extracted with ethyl acetate (500 ml). The combined organic phases were dried over sodium sulfate and concentrated. The residue was purified by column chromatography on silica gel (eluent: cyclohexane/ethyl acetate 2:1) to give 3-amino-4-cyano-N-[2,6-dimethyl-4-(1-trifluoromethyl-vinyl)-phenyl]-benzamide (4.47 g, 81% yield) which was used without further purification. LC/MS (Method A): 360 (MH$^+$); RT: 1.82.

Example I6

Preparation of 3-amino-N-{4-[3-(4-chloro-phenyl)-5-trifluoromethyl-4,5-dihydro-isoxazol-5-yl]-2,6-dimethyl-phenyl}-4-cyano-benzamide

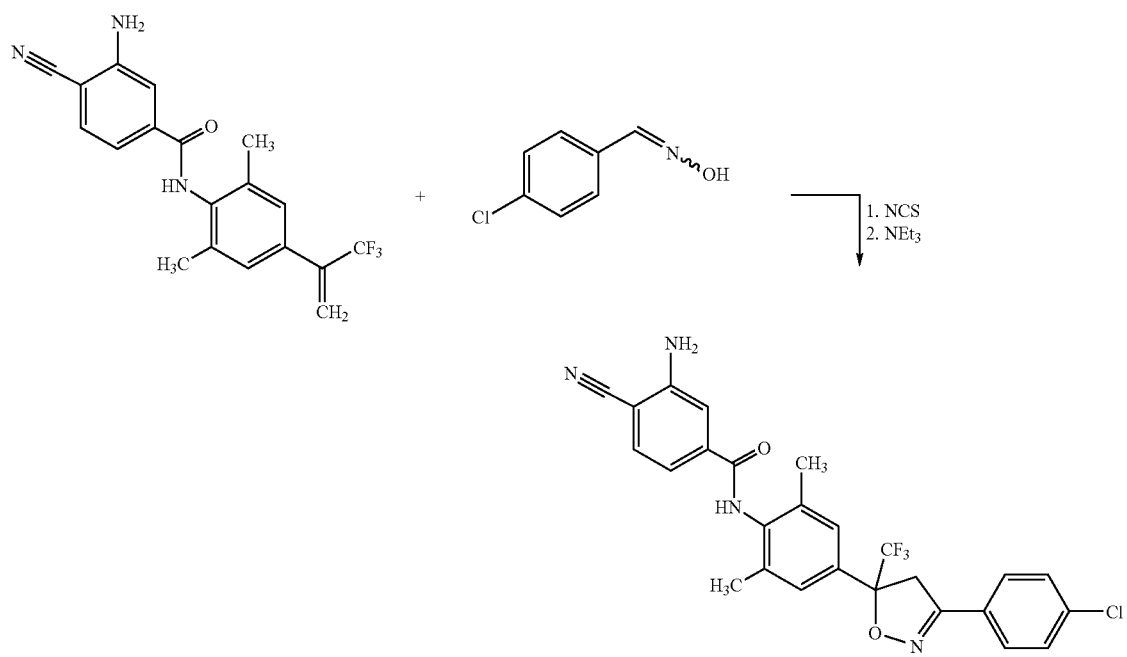

4-Chloro-benzaldehyde oxime (6.64 g, 42.70 mmol) and N-chlorosuccinimide ("NCS") (5.70 g, 42.70 mmol) were dissolved in N,N-dimethylformamide (40 ml). The reaction mixture was stirred at ambient temperature for 90 minutes. A solution of 3-amino-4-cyano-N-[2,6-dimethyl-4-(1-trifluoromethyl-vinyl)-phenyl]-benzamide (4.4 g, 12.20 mmol) (Example I5) and triethylamine (5.95 mL, 0.66 mmol) in N,N-dimethylformamide (40 ml) was added and the reaction mixture was stirred at ambient temperature for 18 hours. The reaction mixture was diluted with water (500 ml) and ethyl acetate (500 ml) and the phases were separated. The organic phase was washed twice with water and the aqueous phases were extracted once with ethyl acetate. The combined organic phases were dried over sodium sulfate and concentrated. The residue was purified by column chromatography on silica gel (eluent: cyclohexane/ethyl acetate 3:1) to give 3-amino-N-{4-[3-(4-chloro-phenyl)-5-trifluoromethyl-4,5-dihydro-isoxazol-5-yl]-2,6-dimethyl-phenyl}-4-cyano-benzamide (3.67 g, 59% yield). LC/MS (Method A): 513 (MH$^+$); RT: 2.04. $^1$H-NMR (CDCl$_3$, 400 MHz): 7.62 (m, 3H), 7.45 (d, 1H), 7.40 (m, 2H), 7.36 (s, 2H), 7.31 (s, 1H), 7.18 (d, 1H), 4.63 (s, 2H), 4.08 (d, 1H), 3.76 (d, 1H), 2.30 (s, 6H) ppm.

Example P1

Preparation of N-{4-[3-(4-chloro-phenyl)-5-trifluoromethyl-4,5-dihydro-isoxazol-5-yl]-2,6-dimethyl-phenyl}-4-cyano-3-(4-nitro-benzoylamino)-benzamide (Compound No. A1 of Table A)

To a solution of 3-amino-N-{4-[3-(4-chloro-phenyl)-5-trifluoromethyl-4,5-dihydro-isoxazol-5-yl]-2,6-dimethyl-phenyl}-4-cyano-benzamide (0.144 mg, 0.77 mmol) (Example I6) in tetrahydrofuran (4 ml) was added pyridine (0.128 ml, 1.50 mmol). 4-Nitro-benzoyl chloride (0.144 g, 0.77 mmol) was added under vigorous stirring. The reaction mixture was stirred at ambient temperature for 2 hours. Aqueous sodium hydrogen carbonate (saturated) was added and the phases were separated. The aqueous phase was extracted twice with ethyl acetate. The combined organic extracts were dried over sodium sulfate and concentrated. The residue was purified by column chromatography on silica gel (eluent:cyclohexane/ethyl acetate ratio 2:1) to give Compound No. A1 of Table A (0.323 g, 84% yield). $^1$H-NMR (CDCl$_3$, 400 MHz): 9.03 (s, 1H), 8.71 (s, 1H), 8.39 (dd, 2H), 8.09 (dd, 2H), 7.90 (m, 2H), 7.83 (d, 1H), 7.62 (m, 2H), 7.41 (m, 2H), 7.38 (s, 2H), 4.06 (d, 1H), 3.77 (d, 1H), 2.32 (s, 6H) ppm.

The following compounds were made using an analogous procedure:

N-{4-[3-(4-Chloro-phenyl)-5-trifluoromethyl-4,5-dihydro-isoxazol-5-yl]-2,6-dimethyl-phenyl}-4-cyano-3-(benzoylamino)-benzamide (Compound No. A2 of Table A) (0.248 g, 70% yield). $^1$H-NMR (CDCl$_3$, 400 MHz): 9.05 (s, 1H), 8.68 (s, 1H), 8.27 (s, 1H), 7.88 (dd, 2H), 7.83 (dd, 1H), 7.71 (d, 1H), 7.62 (m, 3H), 7.52 (m, 2H), 7.41 (m, 2H), 7.32 (s, 2H), 4.05 (d, 1H), 3.77 (d, 1H), 2.28 (s, 6H) ppm.

N-{4-[3-(4-Chloro-phenyl)-5-trifluoromethyl-4,5-dihydro-isoxazol-5-yl]-2,6-dimethyl-phenyl}-4-cyano-3-(4-fluoro-benzoylamino)-benzamide (Compound No. A3 of Table A) (0.349 g, 94% yield). $^1$H-NMR (CDCl$_3$, 400 MHz): 9.17 (s, 1H), 8.50 (s, 1H), 8.12 (m, 2H), 7.98 (m, 2H), 7.90 (m,

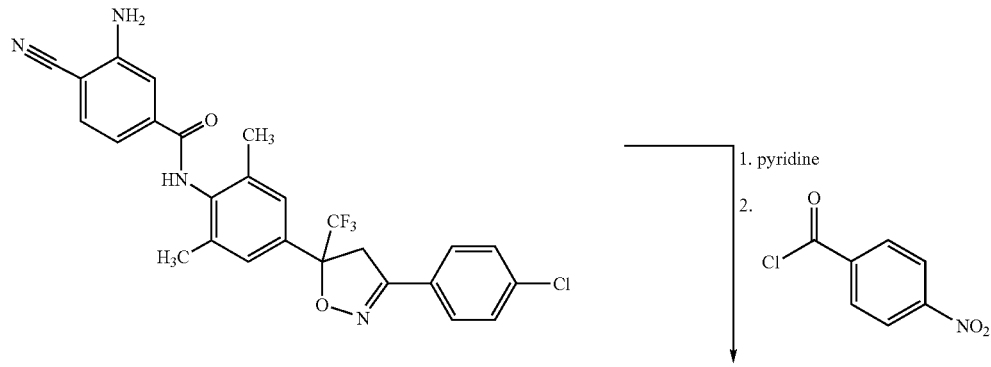

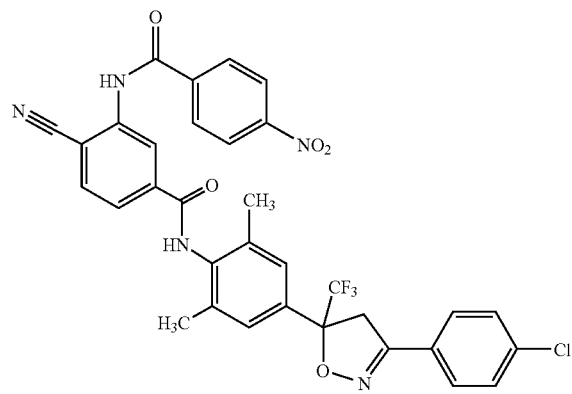

1H), 7.82 (m, 2H), 7.62 (m, 2H), 7.41 (m, 3H), 7.26 (m, 1H), 7.18 (m, 2H), 4.07 (d, 1H), 3.77 (d, 1H), 2.36 (s, 6H) ppm.

Example P2

General Method for Preparing the Compounds of the Invention in Parallel

This general method was used to prepare a number of compounds (Compound No. A4 to A21 of Table A) in parallel.

Solution A was prepared by dissolving the amino derivative (0.65 mmol), 3-amino-N-{4-[3-(4-chloro-phenyl)-5-trifluoromethyl-4,5-dihydro-isoxazol-5-yl]-2,6-dimethyl-phenyl}-4-cyano-benzamide for Compound No. A4 to A21 of Table A (Example I6), in toluene (7.8 ml).

Solution B was prepared by dissolving the acid chloride (1 mol), for example 2-fluorobenzoyl chloride for Compound No. A4 of Table A, in toluene (8 ml).

Solution A (0.3 ml, 25 μmol) was put in a well and solution B (0.4 ml, 50 μmol), and diisopropylethylamine (Hunig's Base) (30 μl, 150 μmol) were added successively. The mixture was heated to 55° C. for 16 hours. Then the mixture was diluted with acetonitrile (0.6 ml) and a sample was used for the LC-MS analysis. The remaining mixture was further diluted with acetonitrile/dimethylformamide (4:1, 0.8 ml) and purified by HPLC to give the desired compound.

The following methods were used for LC-MS analysis:

Method A: (Agilent HP 1100 HPLC) with the following HPLC gradient conditions (Solvent A: 0.05% of formic acid in water; Solvent B: 0.04% of formic acid in acetonitrile/methanol (4:1))

| Time (minutes) | A (%) | B (%) | Flow rate (ml/min) |
|---|---|---|---|
| 0 | 95 | 5 | 1.7 |
| 2.0 | 0 | 100 | 1.7 |
| 2.8 | 0 | 100 | 1.7 |
| 2.9 | 95 | 5 | 1.7 |
| 3.1 | 95 | 5 | 1.7 |

Type of column: Phenomenex Gemini C18; Column length: 30 mm; Internal diameter of column: 3 mm; Particle Size: 3 micron; Temperature: 60° C.

Method B: (Agilent 1100er Series) with the following HPLC gradient conditions (Solvent A: 0.1% of formic acid in water/acetonitrile (9:1); Solvent B: 0.1% of formic acid in acetonitrile; Solvent C: 0.1% formic acid in water; Solvent D: 0.1% formic acid in water)

| Time (minutes) | A (%) | B (%) | C (%) | D (%) | Flow rate (ml/min) |
|---|---|---|---|---|---|
| 0 | 90 | 10 | 0 | 0 | 1.7 |
| 2.5 | 0 | 100 | 0 | 0 | 1.7 |
| 2.8 | 0 | 100 | 0 | 0 | 1.7 |
| 2.9 | 90 | 10 | 0 | 0 | 1.7 |

Type of column: Water atlantis dc18; Column length: 20 mm; Internal diameter of column: 3 mm; Particle Size: 3 micron; Temperature: 40° C.

TABLE A

Compounds of formula (Ia):

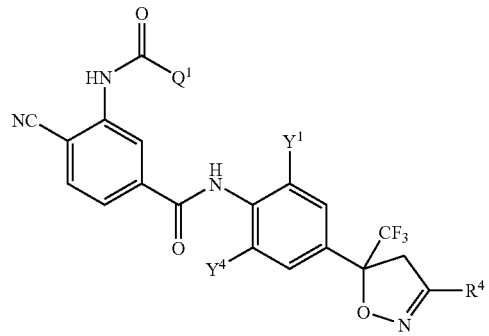

(Ia)

| Compound No. | $Q^1$ | $Y^1$ | $Y^4$ | $R^4$ | RT (min) | MH+ | LC/MS Method |
|---|---|---|---|---|---|---|---|
| A1 | 4-nitro-phenyl- | Me | Me | 4-chloro-phenyl | 2.13 | 662/664 | A |
| A2 | phenyl- | Me | Me | 4-chloro-phenyl | 2.13 | 617/619 | A |
| A3 | 4-fluoro-phenyl- | Me | Me | 4-chloro-phenyl | 2.14 | 635/637 | A |
| A4 | 2-fluoro-phenyl- | Me | Me | 4-chloro-phenyl | 2.2 | 635.1 | B |
| A5 | 2-methyl-phenyl- | Me | Me | 4-chloro-phenyl | 2.2 | 631.2 | B |
| A6 | 2-chloro-phenyl- | Me | Me | 4-chloro-phenyl | 2.2 | 651.1 | B |
| A7 | 4-cyano-phenyl- | Me | Me | 4-chloro-phenyl | 2.1 | 642.1 | B |
| A8 | 2-methyl-thio-4-trifluoro-methyl-phenyl- | Me | Me | 4-chloro-phenyl | 2.3 | 731.1 | B |
| A9 | 5-chloro-2-fluoro-phenyl | Me | Me | 4-chloro-phenyl | 2.3 | 669.1 | B |
| A10 | 2-chloro-4-nitro-phenyl | Me | Me | 4-chloro-phenyl | 2.2 | 696.1 | B |
| A11 | furan-2-yl- | Me | Me | 4-chloro-phenyl | 2.1 | 607.1 | B |
| A12 | 4-trifluoro-methoxy-phenyl | Me | Me | 4-chloro-phenyl | 2.3 | 701.1 | B |
| A13 | 4-fluoro-3-trifluoro-methyl-phenyl- | Me | Me | 4-chloro-phenyl | 2.3 | 703.1 | B |
| A14 | 4-trifluoro-methyl-phenyl- | Me | Me | 4-chloro-phenyl | 2.2 | 685.1 | B |
| A15 | 2-trifluoro-methoxy-phenyl- | Me | Me | 4-chloro-phenyl | 2.2 | 701.1 | B |
| A16 | 2-trifluoro-methyl-phenyl- | Me | Me | 4-chloro-phenyl | 2.2 | 685.1 | B |

TABLE A-continued

Compounds of formula (Ia):

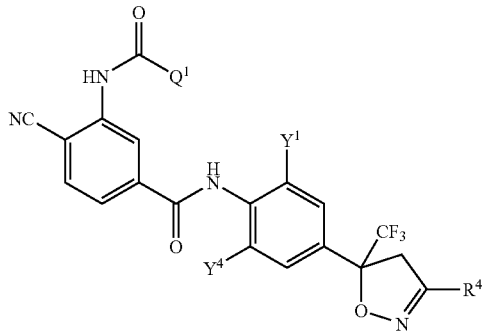

(Ia)

| Compound No. | $Q^1$ | $Y^1$ | $Y^4$ | $R^4$ | RT (min) | $MH^+$ | LC/MS Method |
|---|---|---|---|---|---|---|---|
| A17 | 2-chloro-4-fluoro-phenyl- | Me | Me | 4-chloro-phenyl- | 2.2 | 669.1 | B |
| A18 | 4-methyl-thiadiazol-5-yl- | Me | Me | 4-chloro-phenyl- | 2.1 | 639.1 | B |
| A19 | 2,3-difluoro-phenyl- | Me | Me | 4-chloro-phenyl- | 2.18 | 653.1 | B |
| A20 | 4-methoxy-carbonyl-phenyl- | Me | Me | 4-chloro-phenyl- | 2.1 | 675.2 | B |
| A21 | 2-fluoro-5-trifluoro-methyl-phenyl- | Me | Me | 4-chloro-phenyl- | 2.3 | 703.1 | B |

Biological Examples

This Example illustrates the pesticidal/insecticidal properties of compounds of formula (I). Tests were performed as follows:

Spodoptera littoralis (Egyptian Cotton Leafworm):
Cotton leaf discs were placed on agar in a 24-well microtiter plate and sprayed with test solutions at an application rate of 200 ppm. After drying, the leaf discs were infested with 5 L1 larvae. The samples were checked for mortality, feeding behaviour, and growth regulation 3 days after treatment (DAT).
The following compounds gave at least 80% control of Spodoptera littoralis: A1, A2, A3, A4, A5, A6, A10, A13, A17, A19.

Heliothis virescens (Tobacco Budworm):
Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.
The following compounds gave at least 80% control of Heliothis virescens: A1, A2, A3, A4, A5, A6, A7, A9, A10, A11, A12, A14, A17, A18, A19, A21.

Plutella xylostella (Diamond Back Moth):
24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.
The following compounds gave at least 80% control of Plutella xylostella: A1, A2, A3, A5, A6, A7, A10, A17, A18, A19.

Diabrotica balteata (Corn Root Worm):
A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.
The following compounds gave at least 80% control of Diabrotica balteata: A1, A2, A3, A5, A15, A16, A18, A19.
Compound Nos. A8 and A20 of Table A were tested using the same protocols and showed little or no damage to the test organisms under the test conditions.

The invention claimed is:
1. A compound of formula (I)

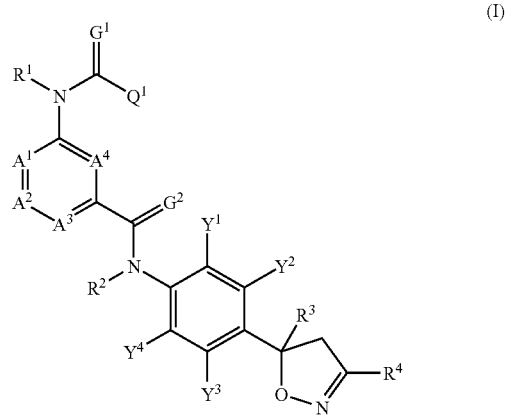

(I)

wherein
$A^1, A^2, A^3$ and $A^4$ are independently of one another C—$R^5$, C—$R^6$ or nitrogen, provided that at least one of $A^1, A^2, A^3$ and $A^4$ is C—$R^5$ and no more than two of $A^1, A^2, A^3$ and $A^4$ are nitrogen;
$G^1$ and $G^2$ are independently of each other oxygen or sulfur;
$R^1$ and $R^2$ are independently of each other hydrogen, $C_1$-$C_4$alkyl or $C_1$-$C_4$alkylcarbonyl;

R³ is hydrogen, C₁-C₆alkyl, C₁-C₆haloalkyl, C₃-C₆cycloalkyl-C₁-C₄-alkyl-, C₁-C₄alkoxy-C₁-C₄-alkyl-, C₁-C₄haloalkoxy-C₁-C₄-alkyl-, C₁-C₄alkylthio-C₁-C₄-alkyl-, C₁-C₄haloalkylthio-C₁-C₄-alkyl-, C₃-C₈cycloalkyl, C₃-C₈halocycloalkyl, phenyl or phenyl substituted by one to five substituents R⁷, which may be the same or different, 2-naphthyl or 2-naphthyl substituted by one to five substituents R⁷, which may be the same or different, or heterocyclyl or heterocyclyl substituted by one to five substituents R⁷, which may be the same or different;

R⁴ is hydrogen, halogen, cyano, C₁-C₆alkyl, C₁-C₆haloalkyl, C₃-C₆cycloalkyl-C₁-C₄-alkyl-, C₁-C₄alkoxy-C₁-C₄-alkyl-, C₁-C₄haloalkoxy-C₁-C₄-alkyl-, C₁-C₄alkylthio-C₁-C₄-alkyl-, C₁-C₄haloalkylthio-C₁-C₄-alkyl-, C₁-C₄alkylsulfinyl-C₁-C₄-alkyl-, C₁-C₄haloalkylsulfinyl-C₁-C₄-alkyl-, C₁-C₄alkylsulfonyl-C₁-C₄-alkyl-, C₁-C₄haloalkylsulfonyl-C₁-C₄-alkyl-, C₃-C₈cycloalkyl, C₃-C₈halocycloalkyl, C₁-C₆alkoxy, C₁-C₆haloalkoxy, C₁-C₆alkylthio, C₁-C₆haloalkylthio, C₁-C₆alkylsulfinyl, C₁-C₆haloalkylsulfinyl, C₁-C₆alkylsulfonyl, C₁-C₆haloalkylsulfonyl, N,N-di(C₁-C₆)alkylamino, phenyl or phenyl substituted by one to five substituents R⁸, which may be the same or different, or heterocyclyl or heterocyclyl substituted by one to five substituents R⁸, which may be the same or different;

each R⁵ is independently cyano, thiocyanato, aminothiocarbonyl, N—C₁-C₄alkyl-amino-thiocarbonyl or N,N-di-C₁-C₄alkyl-aminothiocarbonyl;

each R⁶ is independently hydrogen, halogen, C₁-C₄alkyl, C₁-C₄haloalkyl or C₁-C₄alkoxy;

Q¹ is aryl or aryl substituted by one to five substituents R⁹, which may be the same or different, or Q¹ is heterocyclyl or heterocyclyl substituted by one to five substituents R⁹, which may be the same or different;

Y¹ and Y⁴ are independently of each other hydrogen, cyano, halogen, C₁-C₄alkyl, C₁-C₄haloalkyl, C₁-C₄alkoxy-C₁-C₄-alkyl, C₁-C₃alkylthio, C₁-C₃haloalkylthio, C₁-C₃alkylsulfinyl, C₁-C₃haloalkylsulfinyl, C₁-C₃alkylsulfonyl or C₁-C₃haloalkylsulfonyl;

Y² and Y³ are independently of each other hydrogen, halogen or C₁-C₄alkyl; and each R⁷, R⁸ and R⁹ is independently cyano, nitro, hydroxy, halogen, C₁-C₄alkyl, C₁-C₄halo-alkyl, C₂-C₄alkenyl, C₂-C₄haloalkenyl, C₂-C₄alkynyl, C₂-C₄haloalkynyl, C₃-C₆cycloalkyl, C₃-C₆halocycloalkyl, C₁-C₃alkoxy, C₁-C₃haloalkoxy, C₁-C₃alkylthio, C₁-C₃haloalkylthio, C₁C₃alkylsulfinyl, C₁-C₃haloalkylsulfinyl, C₁-C₃alkylsulfonyl, C₁-C₃haloalkylsulfonyl, C₁-C₄alkyl-amino, di-(C₁-C₄alkyl)amino, C₁-C₄alkylcarbonyl, C₁-C₄alkylcarbonyloxy, C₁-C₄alkoxy-carbonyl, C₁-C₄alkylcarbonylamino or phenyl;

or a salt or N-oxide thereof.

2. A compound according to claim 1 wherein A¹ is C—R⁵ or C—R⁶.

3. A compound according to claim 1 wherein A² is C—R⁵ or C—R⁶.

4. A compound according to claim 1 wherein A³ is C—R⁵ or C—R⁶.

5. A compound according to claim 1 wherein A⁴ is C—R⁵ or C—R⁶.

6. A compound according to claim 1 wherein one, two or three of A¹, A², A³ and A⁴ are C—R⁵.

7. A compound according to claim 1 wherein G¹ is oxygen.

8. A compound according to claim 1 wherein G² is oxygen.

9. A compound according to claim 1 wherein R¹ is hydrogen, methyl, ethyl or acetyl.

10. A compound according to claim 1 wherein R² is hydrogen, methyl, ethyl or acetyl.

11. A compound according to claim 1 wherein R³ is C₁-C₆alkyl, C₁-C₆haloalkyl, phenyl or phenyl substituted by one to five substituents R⁷, which may be the same or different.

12. A compound according to claim 1 wherein R⁴ is C₁-C₆alkyl, C₁-C₆haloalkyl, phenyl or phenyl substituted by one to five substituents R⁸, which may be the same or different, or heterocyclyl or heterocyclyl substituted by one to five substituents R⁸, which may be the same or different.

13. A compound according to claim 1 wherein each R⁵ is independently cyano, thiocyanato or aminothiocarbonyl.

14. A compound according to claim 1 wherein each R⁶ is independently hydrogen, fluoro, chloro, bromo, methyl, trifluoromethyl or methoxy.

15. A compound according to claim 1 wherein Q¹ is aryl or aryl substituted by one to five substituents R⁹, which may be the same or different, or Q¹ is heteroaryl or heteroaryl substituted by one to five substituents R⁹, which may be the same or different.

16. A compound according to claim 1 wherein Y¹ is cyano, halogen, methyl, ethyl, trifluoromethyl or methoxymethyl.

17. A compound according to claim 1 wherein Y² is hydrogen, chloro, fluoro or methyl.

18. A compound according to claim 1 wherein Y³ is hydrogen, chloro, fluoro or methyl.

19. A compound according to claim 1 wherein Y⁴ is cyano, halogen, methyl, ethyl or trifluoromethyl.

20. A compound of formula (XII)

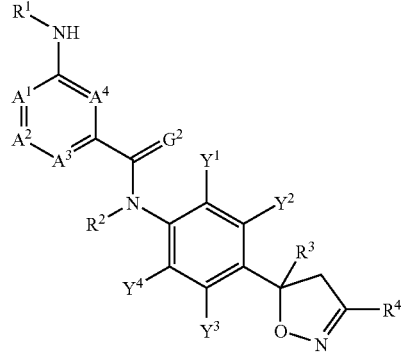

(XII)

wherein A¹, A², A³, A⁴, G², R¹, R², R³, R⁴, Y¹, Y², Y³ and Y⁴ are as defined in claim 1; or a salt or N-oxide thereof;

or a compound of formula (XV)

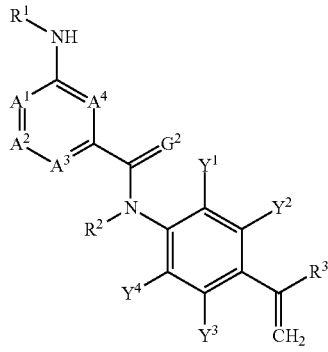

(XV)

wherein $A^1, A^2, A^3, A^4, G^2, R^1, R^2, R^3, Y^1, Y^2, Y^3$ and $Y^4$ are as defined in claim 1; or a salt or N-oxide thereof; or a compound of formula (XVII)

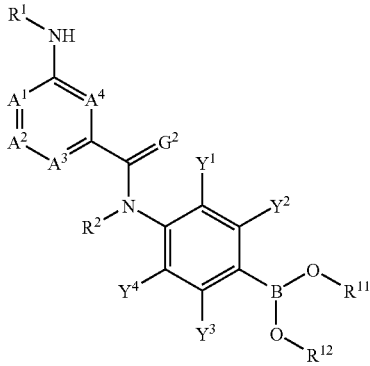

(XVII)

wherein $A^1, A^2, A^3, A^4, G^2, R^1, R^2, Y^1, Y^2, Y^3$ and $Y^4$ are as defined in claim 1, and $R^{11}$ and $R^{12}$ are independently hydrogen, $C_1$-$C_6$alkyl or $C_1$-$C_6$haloalkyl, or $R^{11}$ and $R^{12}$ together with the two oxygen atoms and the boron atom through which they are connected form a five to seven-membered heterocyclyl ring, which can optionally be substituted by one to eight $C_1$-$C_4$alkyl or $C_1$-$C_4$haloalkyl groups; or a salt or N-oxide thereof.

21. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.

22. An insecticidal, acaricidal, nematicidal or molluscicidal composition comprising an insecticidally, acaricidally, nematicidally or molluscicidally effective amount of a compound of formula (I) as defined in claim 1.

* * * * *